United States Patent [19]

Talbot et al.

[11] Patent Number: 5,532,156

[45] Date of Patent: Jul. 2, 1996

[54] HEPATOCYTE CELL LINE DERIVED FROM THE EPIBLAST OF PIG BLASTOCYSTS

[75] Inventors: Neil Talbot, Silver Spring; Caird E. Rexroad, Jr., Gambrills; Vernon G. Pursel, Highland; Anne M. Powell, Bowie, all of Md.

[73] Assignee: The United States of America as represented by the Secretary of Agriculture, Washington, D.C.

[21] Appl. No.: 133,589

[22] Filed: Oct. 8, 1993

[51] Int. Cl.$^6$ .................................................. C12N 5/00
[52] U.S. Cl. ........................ 435/240.2; 435/240.21; 435/240.23; 435/240.243
[58] Field of Search ...................... 435/240.2, 240.21, 435/240.23, 240.243

[56] References Cited

PUBLICATIONS

Talbot et al, In Vitro Cell. Dev. Bio., 29A, 543–544 (Jul. 1993).
Rexroad, "Derivation of Stem Cells for Livestock Species", Dialog Abstract (1992).
Evans et al, Theriongenology, 33, pp. 125–128 (1990).
Strojek et al, Theriongenology, 33, pp. 901–913 (1990).
Piedrahita et al, Theriogenology, 34, pp. 879–901 (1990).
Guguen–Guillouza et al., Exp. Cell. Res., 143: 47–54, 1983.
Perraud et al., Exp. Cell Res., 195: 59–65, 1991.
Langenbach et al., Cancer Research, 39: 3509–3514, 1979.
Aden et al., Nature (London), 282: 615–616, 1970.
Knowles et al., Science, 209: 497–499, 1980.
Evarts et al., Cancer Res., 49: 1541–1547, 1989.
Germain et al., Cancer Res., 48: 4909–4918, 1988.
Colman et al., Am. J. Pathol., 142: 1373–1382, 1993.
Grisham et al., Proc. Soc. Exp. Biol. Med., 240: 270–279, 1993.
Shimaoka et al., Exp. Cell Res., 172: 228–242, 1987.
Michalopoulos et al., In Vitro, 15: 796–806, 1979.
Grisham, J. W. Ann. N.Y. Acad. Sci., 349: 128–137, 1980.
Williams et al., In Vitro, 13: 809–817, 1977.
Berry and Friend, J. Cell Biol., 43: 506–520, 1969.
Caperna et al., J. Anim. Sci., 61: 1576–1586, 1985.
Furukawa et al., in Vitro, 23: 339–348, 1987.
Richardson et al., J. Cell Biol., 40: 236–247, 1969.
Sigal et al., Am. J. Physiol., G139–G148, 1992.
Fausto and Meade, Lab. Invest., 60: 4–13, 1989.
Shiojiri, N., J. Embryol. Exp. Morphol., 79: 149–152, 1981.
Sells et al., In Vitro, 21: 216–220, 1985.

Primary Examiner—Marian C. Knode
Assistant Examiner—Susan M. Dadio
Attorney, Agent, or Firm—M. Howard Silverstein; John Fado; Janelle S. Graeter

[57] ABSTRACT

Continuous cultures of pluripotent parenchymal hepatocytes were derived from the epiblasts of pig blastocysts. The cultures are feeder-dependent and grow slowly with doubling times of 3 to 4 days. They differentiate into large secretory duct-like structures or form small canaliculi. Alternatively, the cells accumulate droplets that stain intensely with oil red O, a lipid-specific stain. α-Fetoprotein and albumin mRNA expression increases as the cells differentiate in culture.

5 Claims, 17 Drawing Sheets

HEPATOCYTE CELL LINE DERIVED FROM THE EPIBLAST OF PIG BLASTOCYSTS

BACKGROUND OF THE INVENTION

1. Field of the Invention

This invention relates to a continuous culture of pluripotent parenchymal hepatocytes derived from the epiblast of pig blastocyst. The culture has been passaged continuously for over 2 years, indicating an infinitely self-renewing cell population. The stem cell characteristics of the hepatocytes indicate that the cells are unique for investigations of liver differentiation and organogenesis.

2. Description of the Prior Art

The continuous secondary culture of normal parenchymal hepatocytes has previously been unsuccessful (Williams et al., *In Vitro*, 13: 809–817, 1977; Guguen-Guillouzo et al., *Exp. Cell Res.*, 143: 47–54, 1983; Perraud et al., *Exp. Cell Res.*, 195: 59–65, 1991). In vitro hepatocyte studies have largely been limited to the use of primary cultures of hepatocytes established after collagenase perfusion of rat or mouse livers (Williams et al., 1977, supra; Berry and Friend, *J. Cell Biol.*, 43: 506–520, 1969). These techniques were also amenable to the establishment of primary hepatocyte cultures in non-rodent species such as the pig (Caperna et al., *J. Anim. Sci.*, 61: 1576–1586, 1985). However, the use of primary cultures is problematic since it is labor intensive and inherently variable. In addition, other epithelial cells, fibroblasts, and macrophages were common "contaminants" in primary liver cell culture and these cells can quickly overgrow or otherwise interfere not only with maintaining cultures but also with experimental manipulations and measurements (Caperna et al., 1985, supra; Furukawa et al., *In Vitro*, 23: 339–348, 1987; Langenbach et al., Cancer Res., 39: 3509–3514, 1979). Moreover, normal liver parenchymal cell activities such as α-fetoprotein (AFP) production, albumin production, and various enzymatic functions were often lost within one to two weeks of establishment in primary culture (Guguen-Guillouzo et al., 1983, supra; Langenbach et al., 1979, supra).

An alternative to normal parenchymal hepatocyte cell culture has been the establishment of numerous human and rodent hepatocarcinoma derived cell lines (Richardson et al., *J. Cell Biol.*, 40: 236–247, 1969; Aden et al., *Nature (London)*, 282: 615–616, 1970). Although several of these hepatoma cell lines were minimally deviated and expressed various proteins representative of normal hepatocyte function, they were likely to be abnormal in several aspects, particularly growth control. For example, some of these cell lines were highly tumorigenic when placed in vivo (Richardson, 1969, supra; Knowles et al., *Science*, 209: 497–499, 1980). Also, while hepatocyte growth factor (HGF) is mitogenic for primary hepatocytes, it has been reported to be cytostatic for the hepatoma cell lines HepG2, Hep3B, and H35 (Higashi and Shima, 1993). Some human hepatoma cell lines also chronically produced hepatitis proteins (Aden et al., 1979, supra; Knowles et al., 1980, supra). Thus, hepatoma derived cell cultures may confuse assessments of normal parenchymal hepatocyte biology in vitro, and in vivo assessments may not be possible. The ability to sustainably culture normal, functional parenchymal hepatocytes in secondary culture is therefore novel and of great value for the routine study of hepatocyte biology.

It has been hypothesized that the liver contains stem cells which support its general long term function, and its regenerative ability (Sigal et al., *M. J. Physiol.*, 263: G139, 1992; Fausto and Meade, *Lab. Invest.*, 60: 4–13, 1989). Stem cells have not been identified, although embryonic phenotypic gene expression, e.g., AFP, was found in some proliferating liver epithelia following the administration of hepatotoxic agents (Fausto et al., Purification and culture of oval cells from rat liver. In: Pretlow and Pretlow, eds. *Cell Separation: Methods and Selected Applications*, Vol. 4. Orlando: Academic Press, 45–77; Evarts et al., *Carcinogenesis*, 8: 1737–1740, 1987). Liver "oval" cells and intrahepatic bile duct cells were also proposed as candidate liver stem cells or facultative stem cells (Sigal et al., 1992, supra; Fausto and Meade, 1989, supra). A consensus of data indicated that liver stem cells would express AFP and albumin and would be capable of differentiating into bile duct cells and parenchymal hepatocytes (Shiojiri, N., *J. Embryol. Exp. Morphol.*, 79: 149–152, 1981; Evarts et al. *Cancer Res.*, 49: 1541–1547, 1989; Germain et al., *Cancer Res.*, 48: 4909–4918, 1988).

Thus, although attempts have been made to establish normal hepatocyte cell lines which are capable of culturing over a long period of time (i.e., years) without losing characteristic activity, accomplishment of this goal has heretofore been unsuccessful.

SUMMARY OF THE INVENTION

A cell line of parenchymal hepatocytes derived from the primary culture of pig epiblast cells has been established which represents the first example of the sustainable culture of normal parenchymal hepatocytes.

Accordingly, it is an object of the invention to provide a novel hepatocyte cell line derived from pig epiblast cells.

It is also an object of the invention to provide a method of preparing the novel cell line from the pig blastocyst.

Other objects and advantages of the invention will become readily apparent from the following description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

The novel cell line was prepared as described by Talbot et al. (In Vitro, 29A: 543–554, 1993) and herein incorporated by reference). It was derived from pig epiblast cells that had been separated from other early embryonic cells and cultured in vitro. The epiblast cell cultures were pluripotent and gave rise to several morphologically distinct cell cultures resembling neural crest cells, muscle cells, fibroblasts, endoderm, polarized epithelium, secretory epithelium and macrophages.

A three-step protocol was used to isolate the epiblast from trophectoderm and primitive endoderm of the blastocyst before culturing. At least two possible benefits were derived from culturing the epiblast free of the attendant heterologous cells of the blastocyst. First, the culture of the intact pig blastocyst results in the attachment and growth of the trophoblast and primitive endoderm, but under these conditions, unlike the mouse blastocyst, the pig epiblast usually does not grow but instead degenerates. In addition, it has been reported (Mummery et al., *Differentiation*, 46: 51–60, 1991) that visceral endoderm can be a potent inducer of mesodermal differentiation for mouse embryonal carcinoma (EC) cells. Thus, the prevention of interaction between the pig epiblast cells and trophectodermal or endodermal cells is considered important in maintaining the epiblast cells in culture. A second reason for culturing an isolated epiblast is that the evaluation of the culture conditions is simplified without the presence of the other blastocyst cells.

Figures 1A, 1B, 1C:
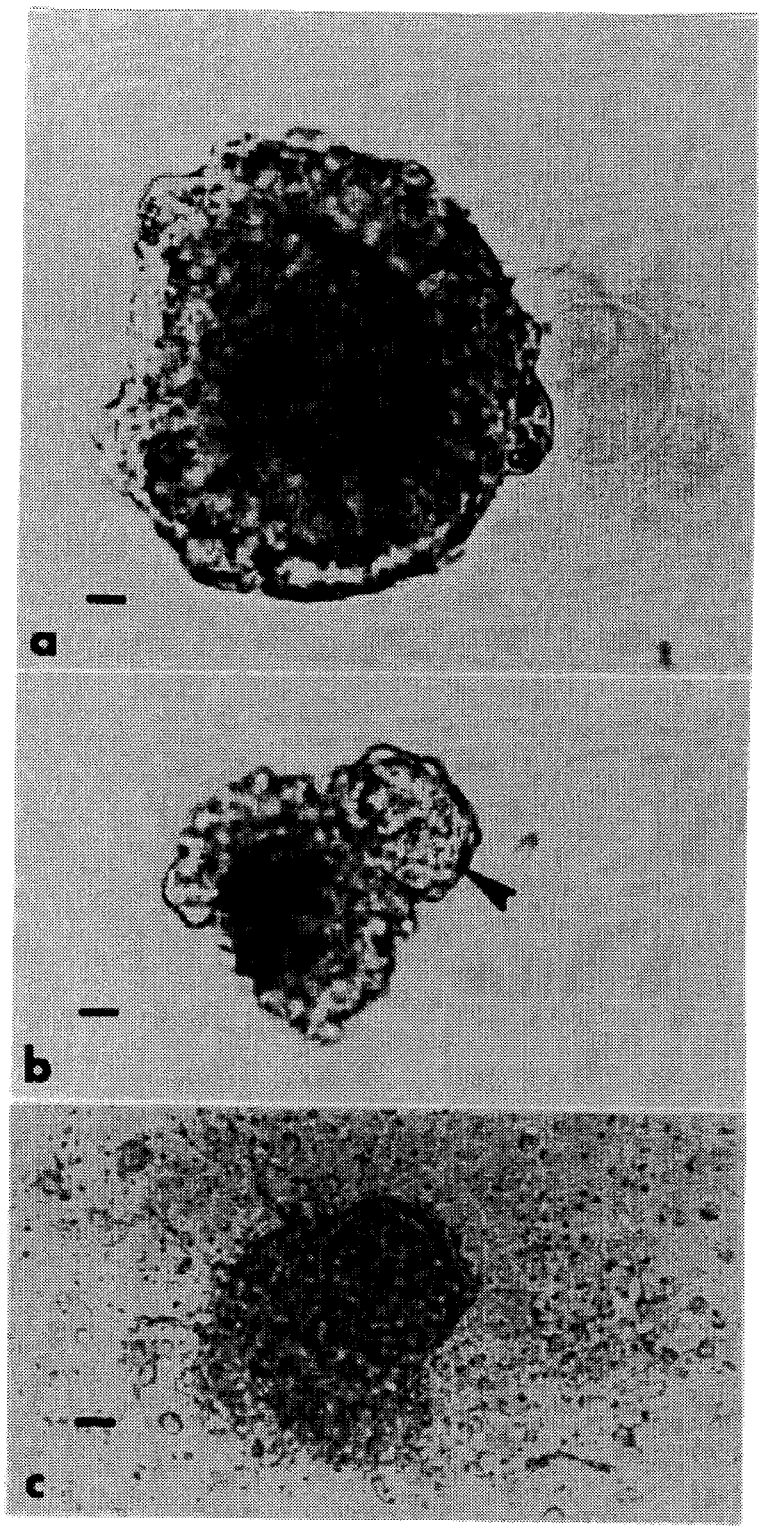
FIG. 1A–1E is photomicrographs of the isolation of pig epiblast from the inner cell mass (ICM) of the blastocyst. a, ICM immediately after immunodissection with epiblast located at the core of the ICM (scale bar, 13 um); b, epiblast exposed by stripping back the primitive endoderm of the ICM with a single cell layer still surrounding the epiblast (scale bar, 26 um); c, ICM after 36 h in STO co-culture (scale bar, 26 um); d, physically dissected pig epiblast (scale bar, 13 um); e, separate co-culture of primitive endoderm with vesicle formation (scale bar, 130 um).
Figures 1D, 1E:
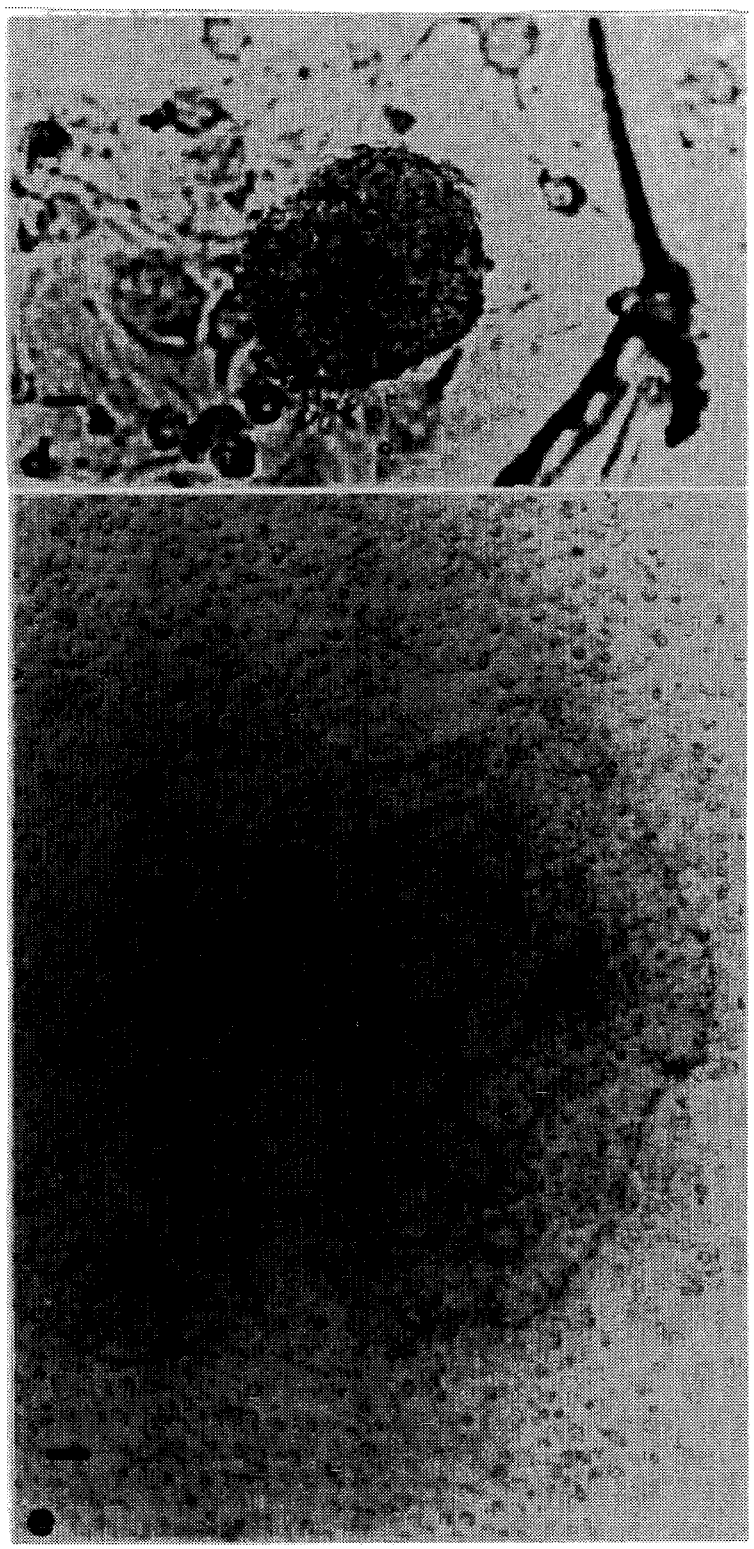
Figure 2:
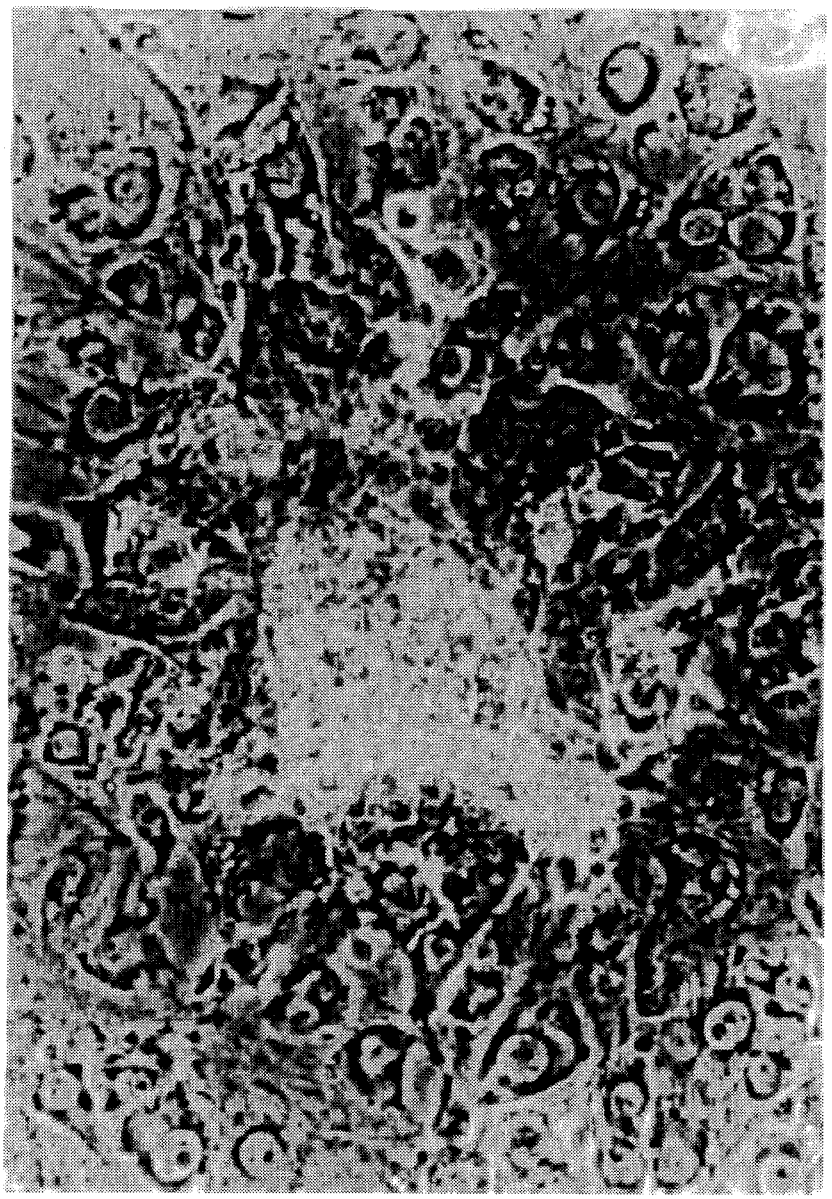
FIG. 2 is a photomicrograph showing a primary colony of pig epiblast cells attaching to STO feeder cell layer, 16 h postdissection (scale bar, 26 um).

Blastocysts collected at 7 to 8 days postestrus were immunodissected to obtain the inner cell mass (ICM) and destroy trophectodermal cells. The pig ICM (PICM) was composed of an inner core surrounded by multiple layers of outer cells (FIGS. 1 and 2). This arrangement is also found in the mouse blastocyst where two rounds of immunodissection have been used to isolate and culture the primitive ectoderm core of the ICM (Hogen et al., *Nature*, 265: 626–629, 1977; Pederson et al., *Nature*, 270: 435–437, 1977). The ICM was cultured for 2 to 3 days on STO feeder cells. The epiblast was then physically dissected free of associated primitive endoderm.

Immunodissection removed most or all of the trophectoderm but little or none of another layer comprising an outer layer of the ICM. This layer completely surrounded the pig epiblast immediately after the immunodissection (FIG. 1a). By mouth-pipetting with a Pasteur pipette slightly smaller in diameter than the ICM, this outer layer could be stripped away from the epiblast core except at one strong attachment point (FIG. 1b). After dissection from the epiblast and culture on STO feeder cells, it grew as colonies of polymorphic epithelial-like cells, which polarized to form domes and vesicles (FIG. 1e). Based on these observations, this outer layer surrounding the epiblast appears to be primitive endoderm in its entirety, necessitating its complete removal from the preparation.

To isolate epiblasts free of endodermal cells, immunodissected ICMs were cultured on STO feeder cells in 10% DMEM(+) for 2 to 3 days. The outer primitive endodermlike cell layer grew radially outward from the centrally located epiblast and surrounded it as a well-organized single-cell layer (FIG. 1c). As with the dissected cells discussed above, the radially spreading endoderm cells produced domes and vesicles (FIG. 1c). The final isolation of the pig epiblast was achieved by a simple physical dissection of the cultured ICM. This was possible because the associated outer layer was only loosely attached after the 2 to 3 days in culture. The epiblast consisted of a well-organized homogenous ball of 50 to 200 cells (FIG. 1d). With this combination of steps, approximately 8 of 10 blastocysts yielded an epiblast free of heterologous cells.

Primary culture of the isolated pig epiblasts on STO feeder cells produced homogeneous colonies whose cells resembled mouse embryonic stem (ES) cells (small round cells with large nuclei and nucleoli, FIG. 2). Pig epiblast cells were approximately the same size as the cells of the D3 mouse ES cell line. Like mouse ES cells, the cells grew as tight clusters either on top of or nested in between the STO feeder cells. Also, the colonies had a rich extracellular matrix which glistened at the colony's edge under phase contrast microscopy (FIG. 2).

Figures 3A, 3B:
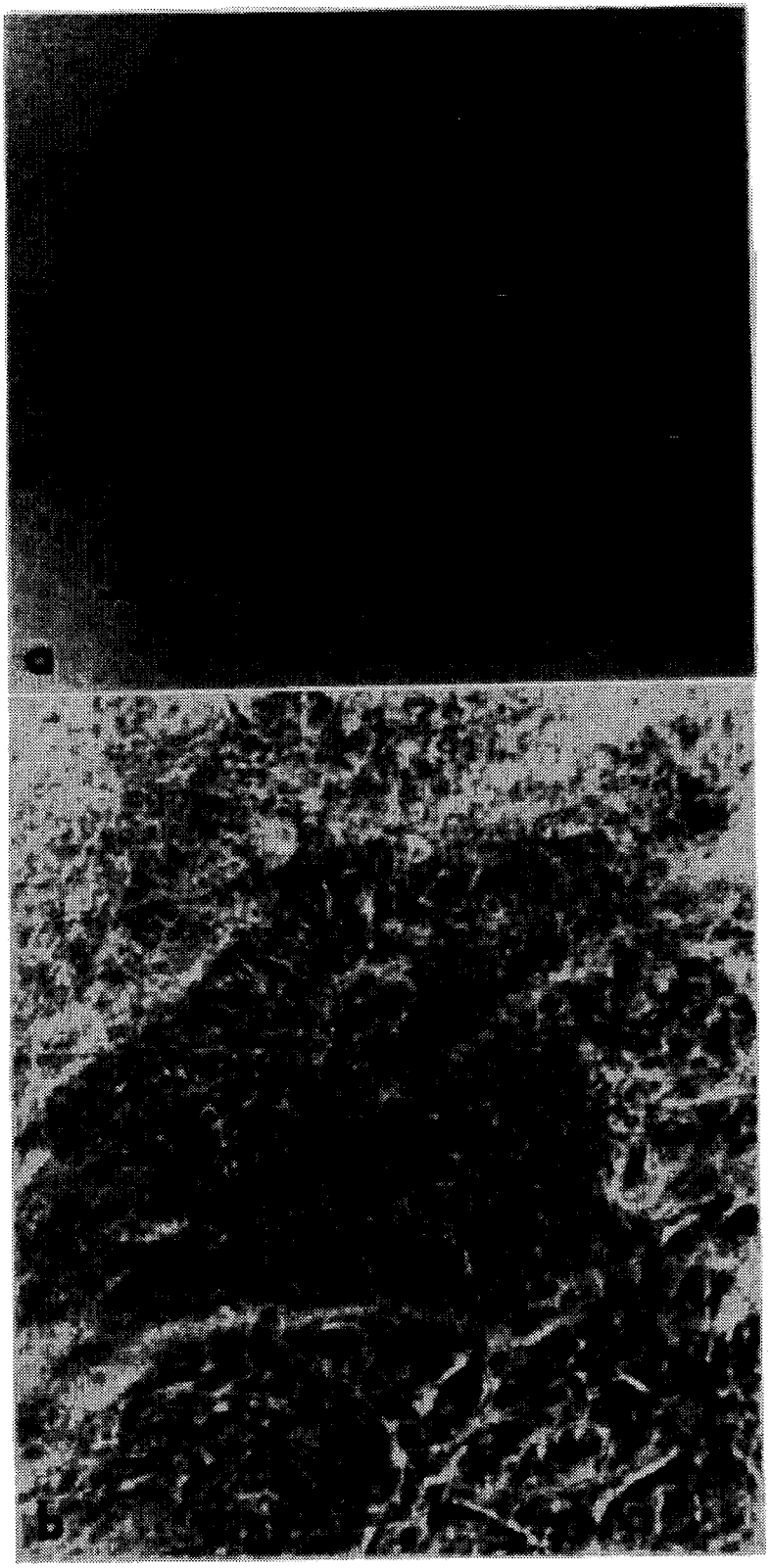
FIG. 3A–3D is photomicrographs of epiblast cell colonies. a, neuroectodermal-like primary pig epiblast colony in STO co-culture (scale bar, 80 um); b, closeup of colony in "a" showing neural rosette formation (scale bar, 15 um); c, epithelial-like primary pig epiblast colony showing distinct heterologous cell-to-cell boundary (scale bar, 130 um); d, closeup of cells in "c" with heterologous cell boundary (scale bar, 26 um).
Figures 3C, 3D:
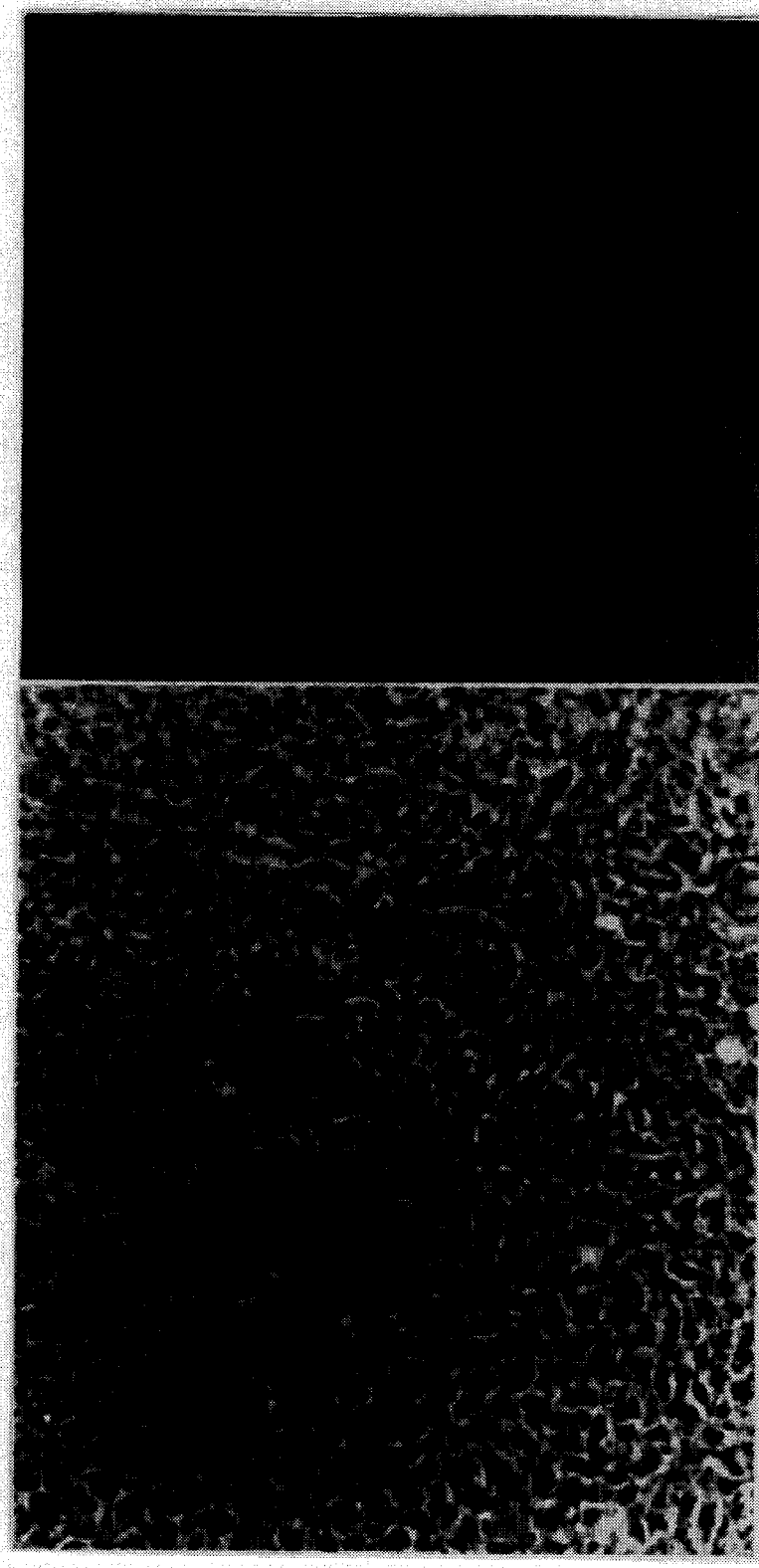

After the initial attachment and spreading of the epiblast cells on STO feeder cells (24 to 36 hours), the colonies progressed in one of several ways. Typical primary colony progression was represented by two separate experiments consisting of six and eight epiblasts. Approximately 10% (1 of 14) of the colonies degenerated into senescent cells which became enlarged, irregularly shaped, and nondividing. This most often occurred when the epiblast was small and consisted of only 10 to 20 cells. Fifty percent (7 of 14) of the epiblast colonies began a rapid growth pattern in which the cells became smaller and were arranged in mushrooming rosettes reminiscent of neural tube formation (FIG. 3a,b). In roughly another 20% (3 of 14), what seemed to be a clonal expansion of an epithelial cell type began within the colonies. These differentiated cells were flat, cuboidal and translucent, with large nuclei but small nucleoli. They rapidly produced a cell sheet which pushed the STO feeder cells and the remaining epiblast cells out of their path, creating an obvious heterologous cell-to-cell boundary at the colony's edge (FIG. 3c,d). The remainder (3 of 14 or about 20%) of the epiblast colonies grew out as a complex of various cell types. Portions of these colonies had cells resembling the two described above (neural rosettes and epithelial-like) along with other unique cell types. Two of these new cell types had prominent nuclei and nucleoli, but each grew in a distinct manner within the colony. One grew as an epithelial-like cell sheet and the other as tight swirled and multilayered group of cells. These colony morphologies became increasingly distinct in their individual character if they were allowed to grow for 1 to 2 weeks or even longer before the first passage of the primary culture was attempted. The vesicle and dome-forming polarized epithelium, which was characteristic of the ICM endoderm, sometimes appeared as a component of the complex colony type. These cells may have differentiated from the epiblast. However, they also may have derived from endoderm cells that were accidentally carried over during the physical dissection of the epiblast from the cultured ICM. Only epiblast colonies composed of either the neuroectodermal-like rosettes of cells or the complex of different cells were passaged for secondary culture.

Figures 4A, 4B:
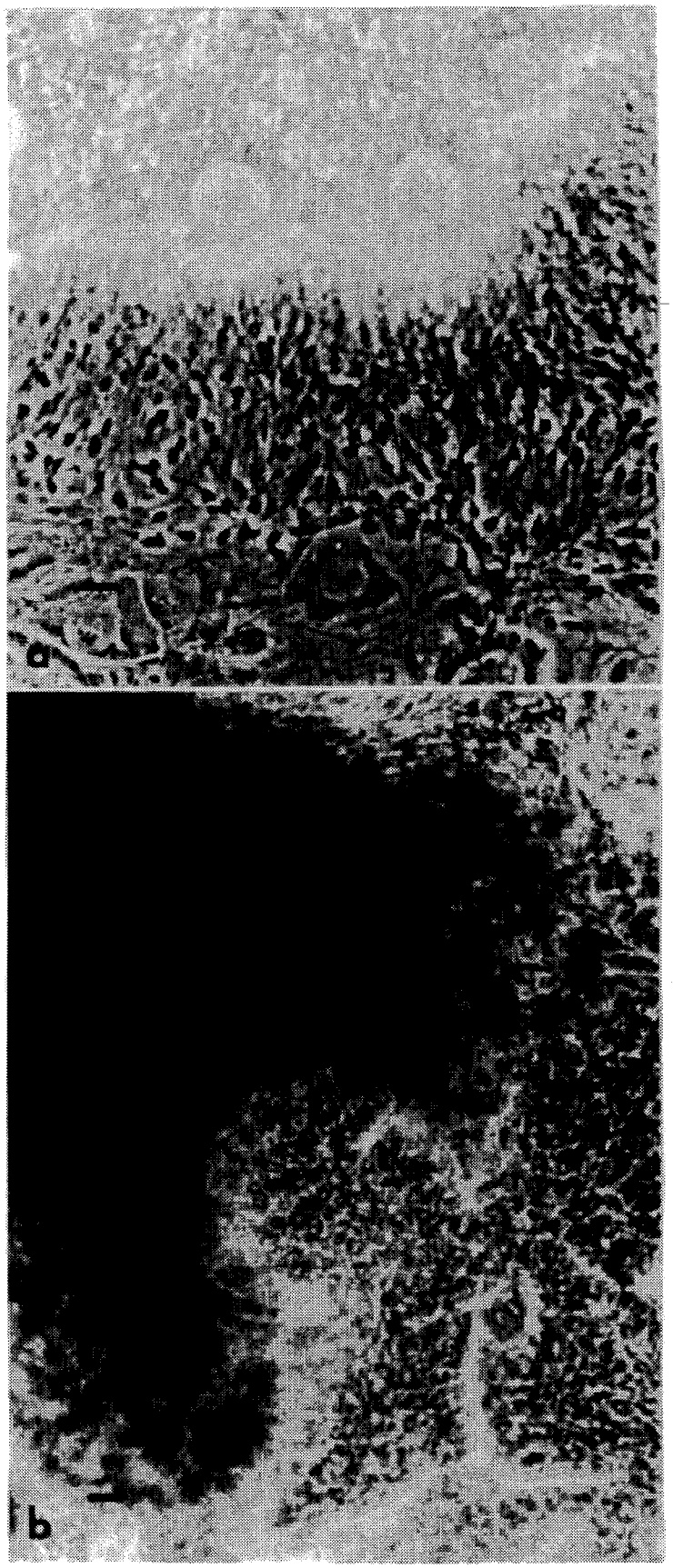
FIG. 4A–4D is photomicrographs showing secondary cultures of pig epiblast colonies. a, secondary neuroectodermal-like pig epiblast colony with neural rosettes and differentiated neuronlike cells (scale bar, 26 um); b, pigment accumulation in neuroectodermal-like secondary colony (scale bar, 15 um); c, PICM-9 contracting muscle cell culture showing multinucleated fused muscle cells (scale bar, 26 um); d, PICM-15 fibroblastic cell culture (scale bar, 26 um).
Figures 4C, 4D:
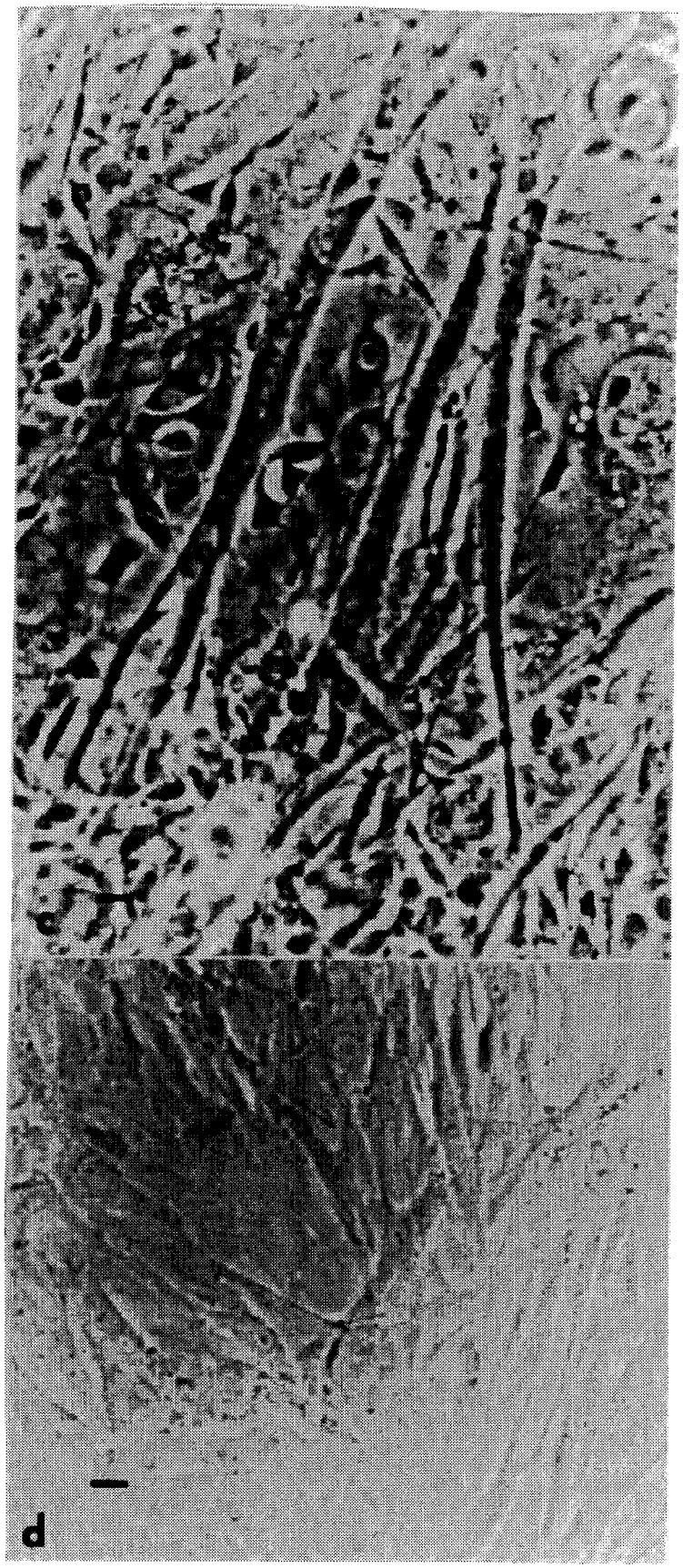
Figures 5C, 5D, 5E:
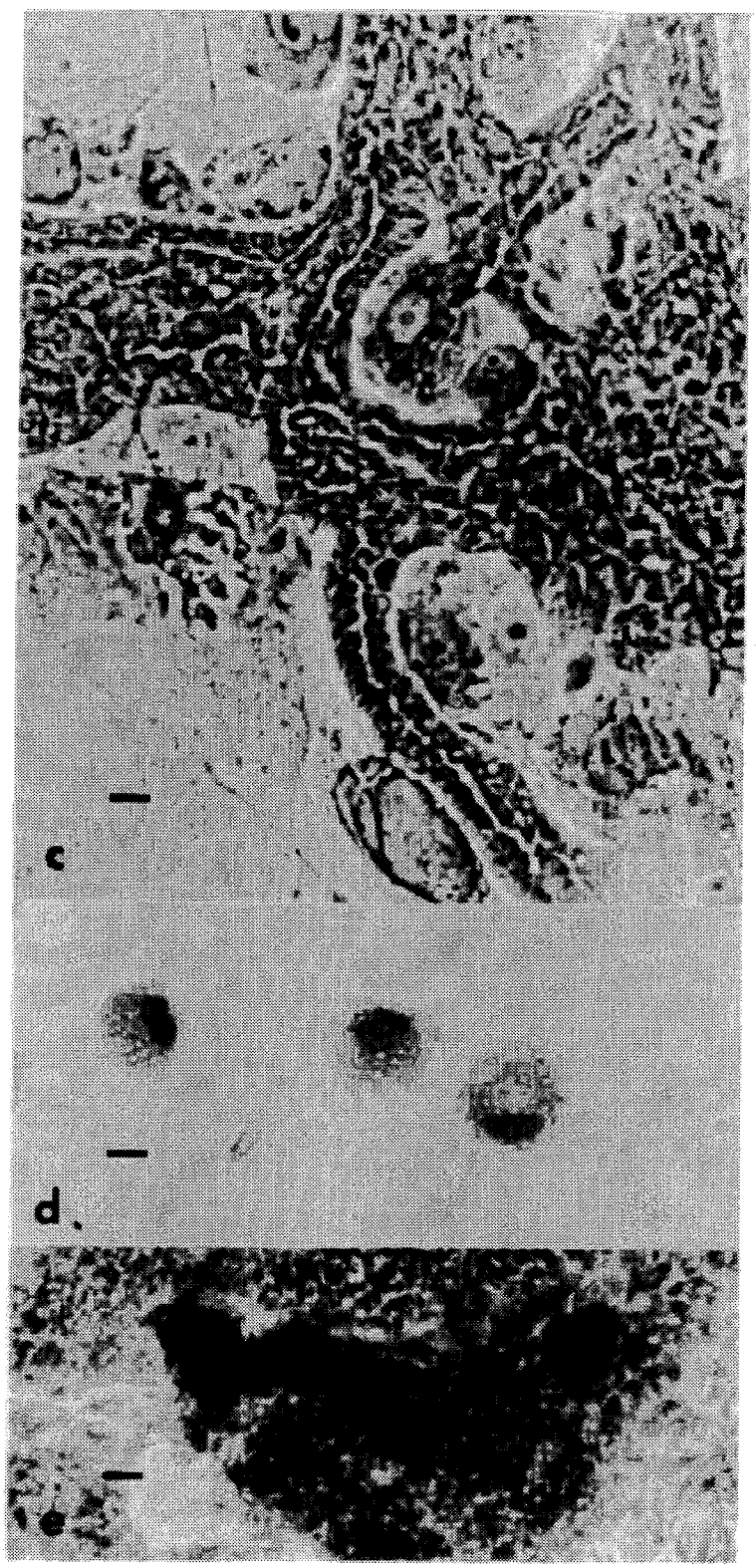
Figures 6A, 6B, 6C:
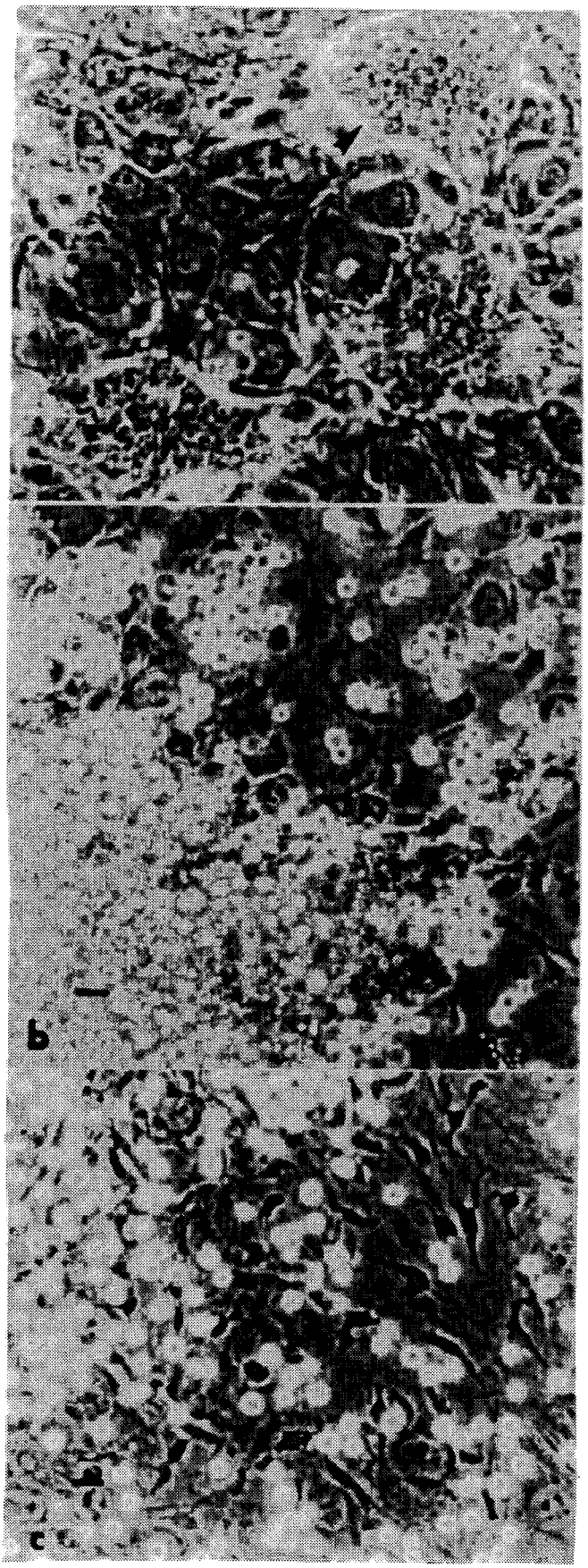
FIG. 6A–6C is photomicrographs showing pig epiblast secondary cell cell cultures. a, PICM-16 cell line at Passage 25; b, PICM-18 secondary colony elaborating round cell type; c, attachment and spreading of round cell type elaborated from PICM-18 secondary colony (scale bars, 26 um).

Secondary cultures of epiblast colonies resulted from subculturing the primary pig epiblast colonies. Numerous primary colonies were lost at passage 1 because of the delicate nature of the epiblast cells. The epiblast colonies composed of small cells which grew as mushrooming rosettes usually gave rise to neuronlike cells upon continuous passage on STO feeder cells. Of seven such colonies cultured, five developed into mass cultures of neuronlike cells (FIG. 4a). These cell cultures were designated PICM-8, 9, 10, 11 and 20 (Table 1). The other two colonies grew very slowly after passage and soon became senescent. Several of the neuronlike epiblast colonies also gave rise to terminally differentiated pigment-producing cells if the cells had clumped during early passage (FIG. 4b and FIG. 5e). For example, one of the five colonies, PICM-9, was passaged almost entirely as grossly clumped groups of cells at passage 2. The majority of PICM-9 clumps failed to grow and instead differentiated into pigmented cells. In addition, after 2 to 3 weeks in maintenance culture, at least four other differentiated phenotypes devloped from the PICM-9 subculture (Table 1). Among these were small fibroblastic cells, neuronlike cells, and one colony which formed a vesicle, the inner surface of which was covered with rapidly beating cilia. Unfortunately, these ciliated cells were not successfully passaged. Also, colonies of multinucleated contracting muscle cells developed and were cloned (FIG. 4c). The PICM-9 muscle cells were small spindle-shaped fibroblasts which grew very rapidly. They spontaneously formed multinucleated contracting muscle cells when seeded at a low concentration on STO feeder cells Six epiblast colonies, which were composed of a complex of cell types, gave rise to several distinct cell cultures after passaging and cloning (Table 1). Neuronlike cells (PICM-12) and fibroblastic cells (PICM-6 and 15, FIG. 4d) were cultured. It was also possible to grow homogeneous cultures of the two cell types with prominent nuclei and nucleoli. The first of these, represented by PICM-16, were very similar to mouse ES cells in appearance (FIG. 6a). PICM-16 grew on top of the STO feeder layer as numerous individual clusters of cells after each passage. After 48 to 72 hours post passage, the PICM-16 cells in the centers of growing colonies flattened into polygonal epithelial-like cells which usually grew over the STO feeder cells. The cells at the periphery of each expanding colony retained their former ES-like appearance. Some dome formation occasionally occurred in cultures of PICM-16 which had reached confluency. Despite treatment with retinoic acid or DMSO, these epithelial-like cultures (PICM-16 and 17) have not shown any other specialized differentiation potential besides formation of polarized epithelium.

Figures 5A, 5B:
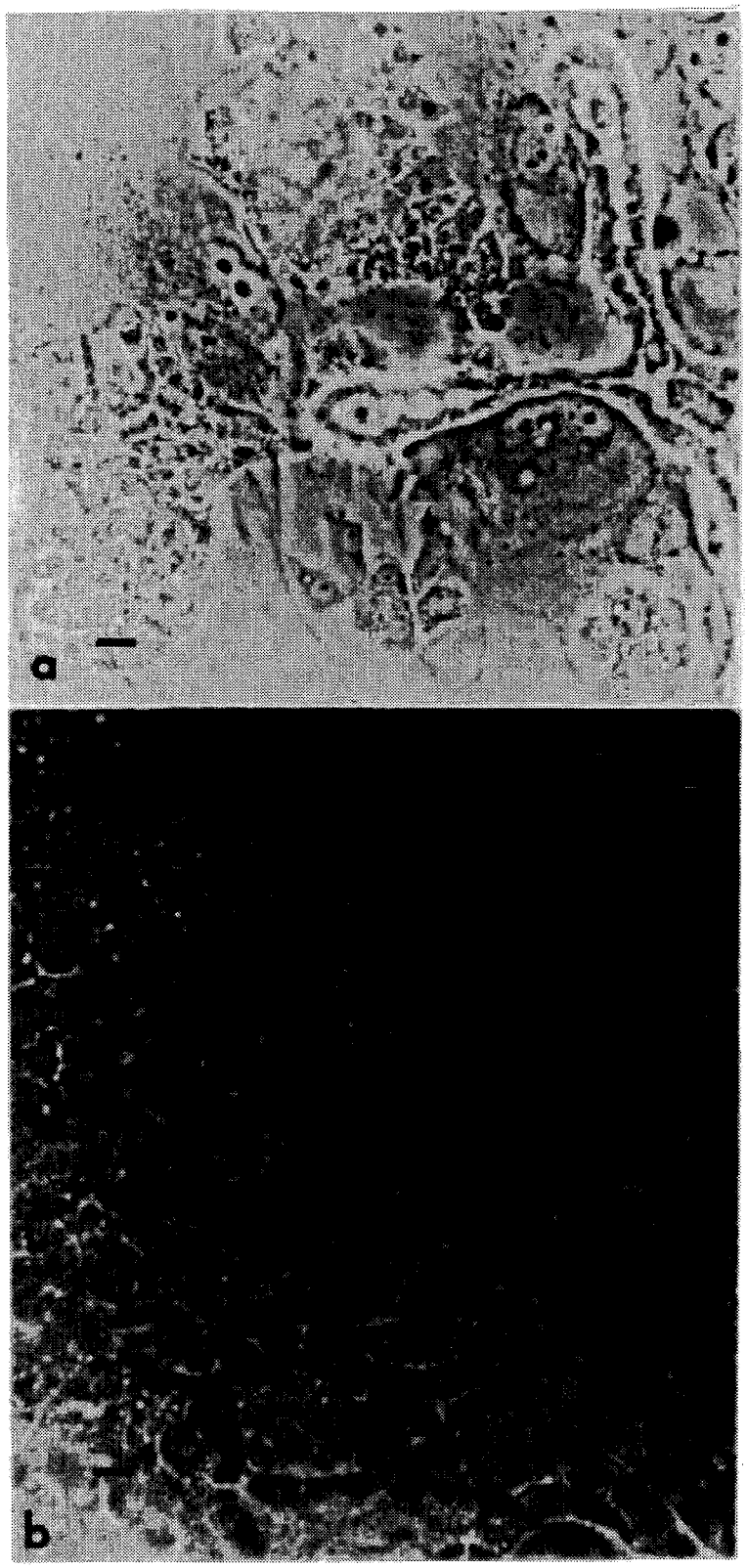
FIG. 5A–5E is photomicrographs showing differentiated cells of secondary pig epiblast cell cultures. a,b, PICM-19 after 2 wk in maintenance co-culture stained with oil red O (a, scale bar, 26 um, and b, scale bar, 15 um); c, PICM-13 after 3 wk in maintenance co-culture, Wright stain (scale bar, 26 um); d, cytospin and Wright stain of PICM-18 round cell type (scale bar, 26 um); e, pigment accumulation in neuroectodermal-like pig epiblast colony (scale bar, 15 um).

The second cell type exhibiting large nuclei and nucleoli, represented by PICM-13, 18 and 19, also grew as numerous individual clusters of cells after each passage (Table 1 and FIG. 5). These cells grew on or between the feeder cells and formed a tubular, glandlike structure if maintained in STO co-culture for a week or more (FIG. 5a,c). The glandlike structures were primarily two-dimensional but often quite extensive and intricate in pattern. The cells assumed a pseudo-columnar orientation as the glandlike formations matured and what appeared to be secretory matter collected at the luminal side of the cells (FIG. 5a,c).

The PICM-13, 18 and 19 cultures also produced a second phenotype (Table 1). After long-term maintenance culture of a month or more, adipogenic processes began in the cells. The accumulated lipid vacuoles were intensely stained by treatment with oil red O stain. The vacuole formation and oil red O staining were not seen in those cells that had undergone differentiation into the glandlike tubules (FIG. 5a,b).

Another cell type appeared, first as round, refractile cells that spewed forth from a central colony of the tubule-adipocyte forming precursor cells (FIG. 6b). Subsequent work has shown, however, that this type occurs independently of the tubule-adipocyte-forming cells, and the concurrence of the two cell types as seen in FIG. 6b was probably coincidental. The round cells were only loosely attached to the feeder cells by small but obvious pseudopods. Over several days to a week in culture, approximately 50% of the cells became firmly attached to the feeder cells and adopted an amoeboid appearance and behavior (FIG. 6c). In both forms, the cells were heavily vacuolated. Grossly, the round cells were similar to maturing adipocytes and some of the cells appeared to have eccentric nuclei as a result of vacuole coalescence (FIG. 6b). However, these cells did not show a tendency to float and were negative for staining with oil red O. Wright-stained cytospin preparations also clearly showed the gross vacuolation, and the cell's profile was most similar to an adipocyte or a plasmacyte (FIG. 5d).

The various PICM cell cultures, with the exception of PICM-16 and PICM-19, could not be propagated under clonal conditions (i.e. from 5 to 10 cells per 1.9-cm² well on STO feeder cells) more than once and thus appear to have a finite doubling potential. With continuous passage on STO co-culture, all of the PICM cell cultures (except PICM-16 and PICM-19) showed a decline in proliferative ability characterisitic of in vitro senescence. At their senescent endpoints (approximately 40 to 50 population doublings) the various PICM cell cultures displayed cytoplasmic vacuolations, perinuclear inclusion bodies, incomplete karyokinesis, and a two- to three-fold increase in overall and nuclear size.

PICM-16 has shown no obvious senescent growth crisis or senescent morphologic changes over the course of greater than 80 passages at alternating 1:5 and 1:10 split ratios. In addition, the PICM-16 cell culture has undergone two successive single-cell clonings. Each clonal PICM-16 cell culture has maintained the same proliferation rate and normal karyotype of the parental culture.

Of the three tubule-forming-adipogenic cell cultures established, only PICM-19 has been continuously passaged. This cell culture grows very slowly and therefore its longevity in STO co-culture remains undefined. However, PICM-19 has now been continuously passaged for over 2 years to greater than 100 cumulative population doublings, with no obvious signs of senescence. While any appropriate feeder cell population may be used successfully for culturing, STO feeder cells are preferred.

Some of the PICM cell cultures were feeder cell-dependent. After only 3 to 4 passages at 1:5 split ratios without STO feeder cells, the neuronlike cells (PICM-8, 9, 10, 11, 12 and 20) flattened, greatly enlarged, collected abundant perinuclear inclusion bodies, stopped dividing, and died. The tubule-adipocyte-forming epithelial cells (PICM-13, 18 and 19) were similarly affected by passage off STO feeder cells. In contrast, the fibroblastic cell cultures (PICM-6 and 15) grew to mass cultures without feeder cells as cell strains exhibiting "normal" Hayflick limits of approximately 40 population doublings. The dome-forming epithelial-like cells (PICM-16) have been maintained without feeder cells for greater than 10 passages. However, the feeder-independent PICM-16 cultures had to be passaged at low split ratios (1:2 or 1:3) to survive and proliferate.

Added human recombinant leukemia inhibitory factor (LIF) at 10 or 20 ng/ml or purified erythroid differentiation factor (EDF) at 50 to 100 ng/ml had no apparent effect on the morphology, maintenance of morphology, or growth of the primary epiblast colony when they were plated on or off STO feeder cells. In contrast, LIF at the same concentration maintained the morphology and growth potential of the D3 mouse ES cells when passaged in the absence of STO cells.

Figure 7:
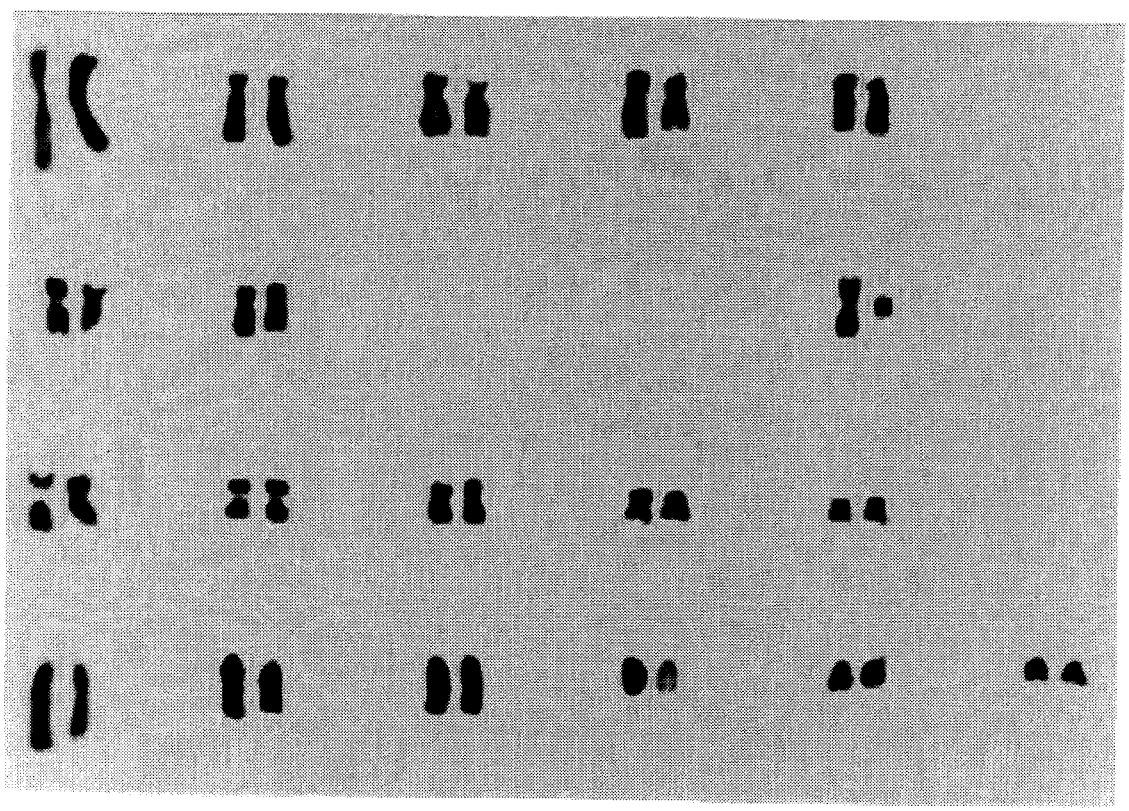
FIG. 7 is a photograph showing Giemsa-stained karyotype of PICM-16 cell line. Male domestic pig (*Sus scrofa*). 2N=38. XY.

Chromosome counts were done on 10 to 20 mitotic spreads from cell cultures maintained for at least 10 passages. All the epiblast-derived cell cultures had the normal porcine complement of 38 chromosomes (35 autosomes and 2 sex chromosomes) with no visible abnormalities, additions, or losses. Karyotypes were constructed of each cell type and all were found to be male (Table 1 and FIG. 7).

The inner core of the pig ICM is the epiblast because the cells derived from it were pluripotent in culture. The outer layers seem to be primitive endoderm because in culture it only gave rise to vesicle and dome-forming cells. A complete layer of cells surrounding the epiblast is incongruent with the view that the endodermal cells in vivo grow over only the side of the epiblast that faces the blastocoelic cavity (Mossman, H. W., Vertebrate fetal membranes. New Brunswick, N.J.: Rutgers University Press, 1987:74–78; Solter and Knowles, PNAS, 72:5099–5102, 1975). Inasmuch as the trophoblast cell layer surrounding the ICM is only one-cell thick, it is probable that no trophoblast cells survive the immunosurgery. This was found to be the case by Solter and Knowles (1975, supra) in their original work with mouse blastocysts. The bulk of the endoderm multilayer can be physically stripped off the pig epiblast core except at one point of strong attachment. This arrangement suggests that the endoderm cells migrated out from the epiblast core as they surrounded it and differentiated.

The pig ICM's outer endoderm layer seemed to be comprised of at least two layers. The endoderm layer, which could be physically stripped off the epiblast core as discussed above, was the outermost layer(s) of endoderm. Left behind was a single cell layer which was closely adherent to the epiblast core (FIG. 2b). When the physically stripped epiblast core was cultured, this innermost endoderm layer also gave rise to a vesicle and dome-forming monolayer. The removal of this innermost layer of endoderm was facilitated by first culturing the intact ICM on STO feeder cells. During the 48-hour culture period, the union between the epiblast core and the innermost endoderm layer was uniformly weakened, thus enabling the physical dissociation necessary for isolating the pure epiblast (FIG. 1e).

TABLE 1

CULTURING PIG EPIBLAST CELLS
PIG EPIBLAST CELL CULTURE DERIVATIONS AND CHARACTERISTICS

| Primary Colony Morphology | Demonstrated Differentiation Potential | Cell Morphology | Cell Culture Designation | Karyotype | PDP[a] on STO feeder | PDP[a] off STO feeder |
|---|---|---|---|---|---|---|
| Complex (25%) | fibroblast-like cells | Fibroblastic | PICM-15 | ND[b] | ~40 | ~40 |
| | | | PICM-6 | ND | | |
| | tubule-forming gland-like cells | Large epithelial (large distinct nucleus and nucleolus) | PICM-13 | 38, XY | | |
| | lipid-filled cells (adipocytes) | | PICM-18 | ND | ~80 | ~3 |

TABLE 1-continued

CULTURING PIG EPIBLAST CELLS
PIG EPIBLAST CELL CULTURE DERIVATIONS AND CHARACTERISTICS

| Primary Colony Morphology | Demonstrated Differentiation Potential | Cell Morphology | Cell Culture Designation | Karyotype | PDP[a] on STO feeder | PDP[a] off STO feeder |
|---|---|---|---|---|---|---|
| | plasmacyte-like cans | | PICM-19 | ND | | |
| | polarized epithelial cells (dome-forming) | ES-like epithelial (large distinct nucleus and nucleolus) | PICM-16 PICM-17 | 38, XY | >300 | undefined |
| Neuroectodermal rosette (40 to 50%) | neuron-like cells | Small fibroblastic (small indistinct nucleus and nucleolus) | PICM-8 | 38, XY | | |
| | pigmented cells (melanocytes) | | PICM-10 | ND | | |
| | | | PICM-11 | ND | ~40 | ~3 |
| | fibroblast-like cells | | PICM-20 | ND | | |
| | neuron-like cells | Small fibroblastic (small indistinct nucleus and nucleolus) | PICM-9 (myocyte) | 38, XY | | |
| | pigmented cells (metanocytes) multinucleated contracting cells (myocytes) fibroblast-like cells | | PICM-9A (neuron-like) PICM-9B (neuron-like) | ND ND | ~40 | ~20 |
| Flat epithelial (25%) | polarized epithelium (dome-forming) | Flat epithelial (small indistinct nucleus and nucleolus) | ND | ND | ND | ND |
| Senescent (10%) | none | Enlarged, disorganized fibroblastic | ND | ND | ND | ND |

[a]PDP = population doubling potential (assuming 100% colony-forming efficiency)
[b]ND = not determined.

Although significant differences in early embryonic development exist between mice and ungulates (Mossman, 1987, supra), under similar culture conditions the morphology of their embryonic stem (ES) cells should be very similar, given the following: a) the ES cells are derived from the ICM at a point before embryonic differentiation; b) they share the same functional attribute of totipotency, and structure often follows function; and c) hamster ES cells and human EC cells are very similar in morphology to mouse ES cells (Andrews et al., I. Cell lines from human germ cell tumours. In: Robertson, E. J., ed. *Teratocarcinomas and embryonic stem cells: a practical approach.* Oxford: IRL Press, 1987: 207–248; and Doetschman et al., *J. Embryol. Exp. Morphol.,* 87: 27–45, 1985). This "ESD-like" morphology was observed in the pig's epiblast cells during the first 48 to 72 h in primary culture. Maintaining this morphology was difficult, however, because as with mouse epiblasts (Hogan et al., 1977, supra), the pig epiblast cells quickly differentiated.

Mouse ES cells often suffer extensive cell death or differentiation if passaged in the absence of feeder cells (Robertson, E. Embryo-derived stem cell lines. In: Robertson, E., ed. *Teratocarcinomas and embryonic stem cells: a practical approach.* Oxford: IRL Press, 1987: 71–112). The cytokine LIF, also known as differentiation inhibitory activity (DIA), is the factor secreted from STO feeder cells which maintains mouse ES cells in an undifferentiated state (Rathjen et al., *Cell,* 62:1105–1114, 1990; Smith and Hooper, *Exp. Cell. Res.,* 145: 458–462, 1983; and Williams et al., *Nature,* 336: 684–687, 1988). EDF (Activin-A) has also been found to suppress the differentiation of mouse EC cells (van den Eijnden-van Raaij et al., *A. Mech. Dev.,* 33: 157–166, 1991). Neither of these cytokines had a differentiation-inhibiting effect on the pig epiblast cultures. This was the case at both the primary colony stage and with the various subcultures established after passage. Furthermore, they did not prevent rapid senescence of the PICM cell cultures when they were removed from culture with STO cells. Thus, under the culture conditions tested, the pig epiblast cells did not respond to LIF in the same manner as mouse epiblast cells. This apparent lack of anti-differentiation or proliferation response to added recombinant LIF has also been observed in certain human EC cell lines (Pera at al., *Differentiation,* 42: 10–23, 1989; P. Andrews, personal communication, 1992) and in the culture of pig and sheep ICM-derived cells (Piedrahita et al., *Theriogenology,* 34: 879–901, 1990). Although there is no direct evidence for the absence of the LIF receptor in the pig epiblast cells, the inability to maintain these cells in an undifferentiated state may depend on up-regulating the expression of the LIF receptor. If the LIF receptor is present, its function may depend on interaction with homologous pig LIF or a synergistic interaction with other growth factors. EDF had a similar lack of effect but this was not unexpected because it also failed to maintain the undifferentiated phenotype of the D3 mouse ES cell line when grown without STO feeder cells.

The lack of response to LIF, either STO-generated or human recombinant, might also result from the inability to effectively disperse the cells of the primary pig epiblast colony. Even when done with very gentle methods, such as lipid-buffered trypsin-EDTA, the cells are easily killed. A critical requirement reported for establishing mouse ES cell lines is the early dispersion and subculturing of the primary epiblast growths (Robertson, 1987, supra). This presumably short-circuits cell-to-cell interactions which lead to differentiation induction. The initial dispersions of the pig epiblast colonies usually resulted in a significant amount of cell clumping, and, analogous to mouse ES and EC cell lines, this clumping may have stimulated differentiation in spite of the presence of LIF.

The pig epiblast cells of the primary and secondary cultures spontaneously differentiated into various cell types, which seem to be mesodermal, neuroectodermal, ectodermal, and endodermal in character. As with some mouse EC cell lines, the final differentiation events of the pig epiblast cultures occurred after several weeks in maintenance culture on STO feeder cells (Nicolas et al., *Cancer Res.,* 36: 4224–4231, 1976). It has long been recognized that the differentiation of various cells is induced by paracrine regulatory interactions or cell-to-cell interactions with mesenchymal cells (Balinsky, B. I., *An introduction to embryology.* Philadelphia: W. B. Saunders, 1970: 566–578; Drew, A. H., *Br. J. Exp. Pathol.,* 4: 46–52, 1923; Gorbstein, C.,

*Exp. Cell. Res.*, 13: 575–587, 1957). The differentiation of the pig epiblast cells may be driven by the STO feeder cells elaborating combinations of growth factors which do not predispose to prevent differentiation. For example, it has been shown that cultured fibroblasts secrete hepatocyte growth factor to the extent that it induces epithelial morphogenensis in co-cultured MDCK cells (Montesano et al., *Cell*, 67: 901–908, 1991). Also, among the known pleiotropic effects of LIF is its ability to promote the differentiation of neural crest cells and hemopoietic cells, to stimulate myoblast proliferation, and to activate hepatocytes (Hilton and Gough, *J. Cell. Biochem.*, 46:21–26, 1991; Mummery, 1991, supra). Given this, it is very possible that co-culture on STO cells contributed to the differentiation observed in the pig epiblast cultures.

The pig epiblast-derived cell cultures, which were non-epithelial in morphology, had a finite life span in STO co-culture of approximately 40 cumulative population doublings (Rohme, D., PNAS, 78: 5009–5013, 1981). In contrast, PICM-16 showed no overt change in growth characteristics or morphology after approximately 300 population doublings in STO co-culture. Also, no gross changes in PICM-16's karyotype has occurred after two successive single cell clonings. Thus, PICM-16 is similar to mouse ES cell lines in being immortal and in retaining a normal male karyotype (Robertson and Bradley. Production of permanent cell lines from early embryos and their use in studying developmental problems. In: Rossant and Pedersen, eds. *Experimental approaches to mammalian embryonic development*. New York: Cambridge University Press, 1986: 475–508). The indefinite growth potential of PICM-16 may be the result of transforming genetic events, and fine band analysis must be done in an attempt to find evidence of any karyotypic abnormalities. Although the propagation of PICM-16 was not rigorously quantitated, a senescent crisis followed by resurgence of a transformed cell population, as is typical in mouse embryonic fibroblast cultures, was not observed in the PICM-16 culture.

Senescence occurred in some of the pig epiblast cultures despite the presence of 2-mercaptoethanol in the medium. 2-Mercaptoethanol has been shown to be essential to the cultivation of some cell types and, in general, is thought to be necessary for the isolation and maintenance of mouse ES cells (Robertson, 1987, supra; Tookey, J. I., PNAS, 72: 73–77, 1975). In addition, mouse embryonic fibroblasts have recently been shown to be protected against senescent crisis in culture if the medium contains inhibitors of serum amine oxidases or 2-mercaptoethanol (Parchment et al., PNAS, 87: 4340–4344, 1990). PICM-16 could be an analogous event to that seen with mouse cells, but in this study, examining epiblast culture, it seems to represent the exception rather than the rule.

The differentiation of the pig epiblast cell cultures was brought about by cell aggregation combined with long-term culture. Those cell cultures (PICM-8, 9, 10, 11, 12 and 21), which start out by forming neuronal-like rosettes of cells, may be committed as neuroectodermal stem cells. As such, they would be expected to be able to form neurons and pigmented cells, which, in fact, they all do, based on morphology. Also, preliminary tests indicate that PICM-8 displays a mitogenic response to LIF and EDF, both of which are known to support the differentiation and maintenance of neuronal cells (Murphy et al., PNAS, 88: 3498–3501, 1991: Schubert et al., *Nature*, 344: 868–870, 1990). The neuroectodermal colony, PICM-9, also gave rise to fibroblasts, contracting muscle, and ciliated epithelium after pronounced clumping of the cells and 6 weeks in maintenance culture. However, this was at passage 2, and it is likely that this degree of pluripotency is lost with continued passage of the cells. The cell cultures that differentiated into glandlike structures or adipocytelike cells (PICM-13, 18, 19) had a distinctive morphology which is typical of parenchymal hepatocytes, thus raising the possibility that these cells represented hepatic stem cells.

The cell line, PICM-16, which is epithelial in character and most closely resembles mouse ES cells, has occasionally formed domes. Although mouse ES cell lines are not known to form domes in culture, a human EC cell line, NEC 14, apparently shares this characteristic with PICM-16 (Haseyawa et al., *Differentiation*, 47: 107–117, 1991). PICM-16 is morphologically similar to the ICM-derived pig cells isolated by other groups. Only limited information has been published on the in vitro or in vivo pluripotency of these other cell cultures (Evans and Kaufman, *Nature*, 292: 154–156, 1981; Evans et al., *Theriogenology*, 33: 125–128, 1990; Notarianni et al., *J. Reprod. Fertil. Suppl.*, 41: 51–56, 1990; Piedrahita, 1990, supra).

The derivation of a round amoeboid cell type is notable. Results obtained with monoclonal antibodies to pig cell surface antigens indicate that the round cells may be of macrophage/granulocyte lineage.

The PICM-19 cells have utility as an in vitro model for fetal hepatocyte functions (e.g., hemopoiesis) and are also useful in experimentation on artificial organ construction and gene therapy. For example, attempts have been made to utilize rat hepatocytes for the construction of bioartificial livers (Nyberg et al., *Cytotechnology*, 10: 205–215, 1992; Li et al., In Vitro *Cell. Dev. Biol.*, 29A: 249–254, 1993) Since pig liver cells are physiologically more closely related to human cells than mouse or rat, the cells described herein have obvious advantages over cells of such origin as well as the obvious advantage of normal cells over tumor cells. The cell line also has significant value as a research reagent, that is, a sustainable fetal liver cell culture. Moreover, it would serve as a valuable source of novel growth factors and pharmaceuticals and for the production of viruses or vaccines (e.g., hepatitis viruses), as well as for the study of liver parasites or of parasites having a stage of development in the liver (e.g., malarial organisms), for in vitro toxicity and metabolism testing of drugs and industrial compounds, for gene therapy experimentation (since the liver is the largest vascular organ of the body), for the construction of artificial translatable livers, and for liver mutagenesis and carcinogenesis studies. In addition, the derivation of the PICM hepatocyte cultures from the pig epiblast demonstrates the possibility of deriving specialized cell types from any mammalian epiblast.

The cell line ARS-PICM-19 was deposited on Jan. 4, 1994 under the Budapest Treaty in the American Type Culture Collection, 12301 Parklawn Drive, Rockville, Md., 20852, as ATCC No. CRL 11519.

The following examples are intended only to further illustrate the invention and are not intended to limit the scope of the invention which is defined by the claims. PICM-19 provides an exemplary representative of a number of hepatocyte cell lines independently prepared from pig blastocysts and having the properties of the novel continuous cell line described herein.

EXAMPLES

EXAMPLE 1

Isolation of Blastocysts and Cell Preparation

Blastocysts were collected 7 to 8 days postestrus by flushing each uterine horn with 20 ml of a modification of the Tyrodes-HEPES (TLH) medium described by Hagen et al. (*J. Anim. Sci.*, 69: 1147–1150, 1991). The isolated hatched blastocysts were incubated in TSH in air at 38° C. until dissection.

A double dissection procedure was carried out. First, immunodissection was performed according to Solter and Knowles (1975, supra). Blastocysts were incubated at 37° C. for 1 hour in rabbit anti-sheep splenocyte serum, prepared as described by Butler (In: Evans and Hollaender, eds. *Genetic engineering of animals: an agricultural perspective*. New York: Plenum Press, 1986: 175–185), and diluted 1:8 in DMEM. After washing 3 times in 10% DMEM, the blastocysts were incubated at 37° C. for about 30 minutes in guinea pig serum (GIBCO, Gaithersburg, Md.) diluted 1:4 in DMEM. Lysed cells were removed by mouth pipette aspirations, and the ICMs were cultured on feeder layers of STO cells for 2 to 3 days.

A physical second dissection was done using 25-gauge hypodermic needles as dissection knives. Isolated epiblasts were co-cultured on STO feeder cells in 10% DMEM(+) [10% DMEM with 2-mercaptoethanol (0.1 mM), nucleoside supplementation (0.01 mM guanosine, 0.03 mM adenosine, 0.01 mM cytidine, 0.01 mM uridine, and 0.01 mM thymidine), nonessential amino acids supplementation (2 times, GIBCO), and glutamine supplementation (1 mM, GIBCO) after the method of Robertson (1987, supra)].

Following dissection, all cells were grown on tissue culture plasticware (Nunc and Falcon). Most cell culture reagents, including fetal bovine serum (FBS), media, phosphate buffered saline (PBS), and trypsin-EDTA (0.025% trypsin, 0.43 mM EDTA) were obtained from GIBCO. STO cells, a transformed mouse fibroblast line, were obtained from the American Type Culture Collection, Rockville, Md., and were propagated in Dulbecco's modified Eagle's medium (DMEM) with high glucose, 10% FBS, and antibiotics (10% DMEM). STO feeder cells were prepared as described by Robertson (1987, supra).

Primary epiblast colonies were passaged by two methods. One method was to physically detach the colonies by a mouth-controlled pipette and wash them through two successive drops of lipid-trypsin. The lipid-trypsin solution consisted of soybean lipid (2 mg/ml) made isotonic by the addition of 10 times Dulbecco's PBS ($Ca^{2+}$-and $Mg^{2+}$-free) and containing 0.01% wt/vol crystallized trypsin. The acidity of the lipid solution was neutralized by the addition of NaOH. After the brief washings, the colony was placed into a final small drop of lipid-trypsin (10 to 20 µl) and incubated for 3 to 5 minutes at 37° C. Trypsin activity was then neutralized by adding an equal volume of FBS or 10% DMEM(+) to the drop. An alternative method was to expose the primary colonies to 1.2 to 2.4 U/ml of dispase 1 in culture medium for 1 to 2 hours at 37° C. With either method, the colonies were disaggregated into small clumps and single cells by repeated aspirations with a P10 Pipetman. Primary and secondary epiblast cultures were grown on STO feeder cells which were 95 to 100% confluent in either 10% DMEM(+) or 15/5 DMEM-M199 [15/5 DMEM-M199 consisted of a 50:50 mixture of DMEM and Medium 199 (GIBCO) containing 15% FBS and 5% bovine calf serum].

EXAMPLE 2

Secondary Cell Cultures

The cells derived from the preparation described in Example 1 were placed in secondary culture by growing on mitomycin C, 10 µg/ml, (Sigma Chemical Company, St. Loius, Mo.) inactivated STO mouse fibroblast feeder cell layers [CRL 1503, American Type Culture Collection (ATCC)] plated at $5 \times 10^4$ cells/cm². The culture medium was a 1:1 mixture of Dulbecco's modified Eagle's medium and Medium 199 with 10% FBS and antibiotics (10% DMEM-199+, GIBCO). Additional supplementation with 2-mercaptoethanol, nonessential amino acids, glutamine and nucleosides was as described in Example 1.

Figure 8A:
FIG. 8A–8D is photomicrographs showing the hepatocyte-like morphology and differentiation of PICM cells in STO co-culture. a, PICM-35, Passage 7, oil red O stain after 3 wk in static culture with differentiation into open lumen ductal structures and intracellular and extracellular accumulations of lipid (scale bar, 88 um); b, PICM-19, Passage 39, with ductal formations without an open lumenal space but with collected secretory material after 2 wk in static culture (scale bar, 44 um); c, PICM-19, Passage 5, in monolayer with biliary canaliculi-like structures between cells after 2 wk in static culture (scale bar, 44 um); d, oil red O stained colony of NIH/3T3 cells undergoing adipogenesis (scale bar, 88 um).
Figure 8B:
Figure 8C:
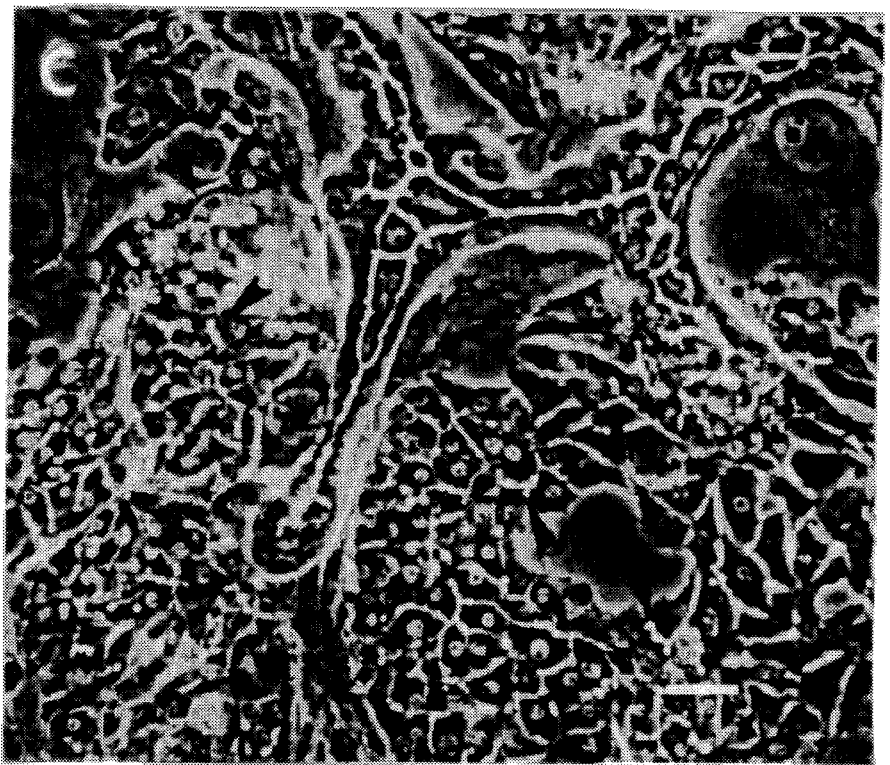

The PICM hepatocyte cell cultures displayed a morphology typical of primary cultured parenchymal hepatocytes (Berry and Friend, 1969, supra; Caperna et al., 1985, supra; Furukawa et al., 1987, supra). The cells were polygonal with well defined cell boundaries. Under phase-contrast microscopy they had dark, granular cytoplasm with large, distinct nuclei and nucleoli (FIG. 8c). Only mononuclear cells were observed. Previously, fetal and neonatal parenchymal hepatocytes were described as mononuclear whereas primary cultures of adult hepatocytes usually contained binuclear cells (Caperna, 1985, supra, Juan et al., *Exp. Cell Res.*, 202: 495–500, 1992). Karyotope analysis of PICM-13 and PICM-19 also showed no evidence of polyploidy and confirmed the porcine origin of the cells. All the cell cultures differentiated to multi-cellular duct-like structures and into colony groupings that either accumulated and secreted lipid or developed spaces between individual cells similar to biliary canaliculi (FIG. 8a,b,c). The ductal and adipogenic differentiation phenotypes appeared to be mutually exclusive and occurred spontaneously over the course of 1 to 3 weeks in static co-culture on STO feeder-layers.

It has been found that in primary parenchymal hepatocyte cultures, small biliary canaliculi often developed within the monolayers (Furukawa, 1987, supra; Barth and Schwartz, PNAS, 79: 4985–4987, 1982). Likewise, small canaliculi of the same size and character developed in the monolayers of the PICM cells (FIG. 8c). Once formed, canaliculi were stable and their associated cells could retain their large polygonal shape for weeks without significant change. However, canaliculi were also observed in areas of the monolayer which eventually proceeded to duct formation and adipogenesis. As can be seen at the top of FIG. 8c, individual canaliculi coalesced to form longer networks of interconnected canaliculi. Final differentiation into a mature ductal structure appeared to occur from these interconnected canaliculi. Duct formation was a terminal differentiation event since the constituent cells would no longer divide and grow if passaged, although they remained viable. Similarly, cultures which differentiated to adipogenesis grew very slowly when passaged and could not be sustainably cultured. In contrast, colonial areas that developed small canaliculi could be cloned and passaged to produce mass cultures without loss of differentiation potential. Thus, the development of canaliculi was non-terminal differentiation which could be a precursor to the terminal ductal or adipogenic differentiation programs.

Phase-contrast microscopy of the fully differentiated duct-like structures showed phase-dense material at the lumenal surface of the structures (FIG. 8a). This arrangement indicates a secretory structure. A modified form of the duct-like differentiation structure occurred in the PICM-19 culture after about 50 population doublings. This formation was characterized by the absence of a "lumenal" space. Instead, the duct-like structures were closed with the cells assuming a distinct pseudo-columnar arrangement. Heavy deposits of secretory matter appeared between the juxtaposed cells over a period of 2 to 3 weeks in static culture (FIG. 8b).

Figure 8D:
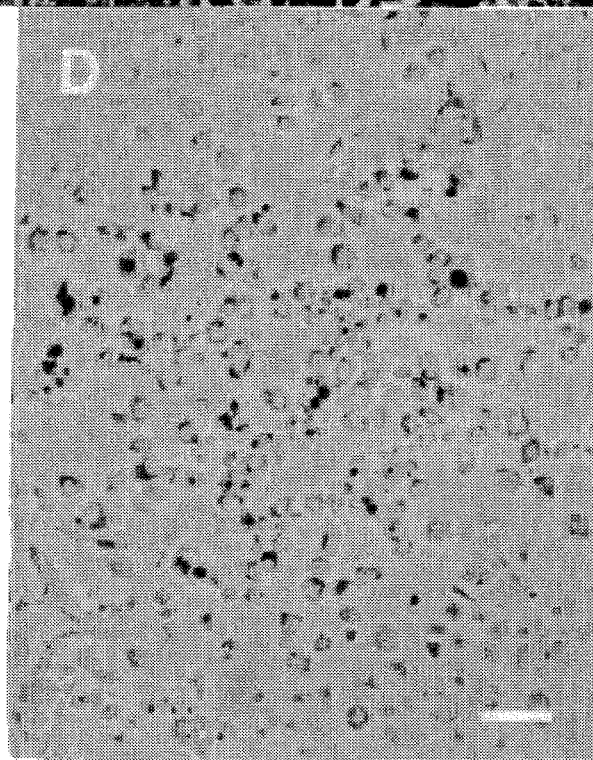

Primary cultures of rodent parenchymal hepatocytes sometimes accumulated lipid, consistent with their lipogenic in vivo function (Richardson et al., 1969, supra; Michalopoulos et al., *Cancer Res*, 42: 4673–4682, 1982). PICM-13, 18, 19, 26, 29 and 35 produced colonies that stained intensely with oil red O (FIG. 8a) indicating lipid sequestration. Although adult porcine liver has little capacity to synthesize and accumulate fatty acids, the enzymatic machinery for de novo fatty acid synthesis is present (Mersmann, H. J., In: Tumbleson, M. E., ed. *Swine in Biomedical Research*, Vol. 2. New York: Plenum Press, 1986: 981–995). The production of triglycerides by the PICM hepatocyte cultures may result from the embryonic nature of the cells or the in vitro culture conditions, i.e., presence/lack of specific hormonal stimuli or possibly basic medium components. The lipid appeared to be actively secreted from the cells since large globules of lipid were often present in the extracellular matrix above the cells to the extent that the cells could no longer be clearly discerned. In contrast, lipid accumulation typically seen in certain fibroblast cultures, such as mouse 3T3 adipocytes, was cell bound, and the cells were prone to detach and float off the substrate because of the buoyancy of the lipid (FIG. 8d). The firm anchorage of the PICM cells undergoing lipid accumulation probably reflects an interconnective cytoskeleton network typical of cultured epithelial cells in general and of parenchymal hepatocytes specifically (Osborn and Weber, *Cell*, 31: 303–306, 1982; Marceau et al., *Can. J. Biochem. Cell Biol.*, 63: 448–457, 1985; Levy et al. *Differentiation*, 39: 185–195, 1988).

EXAMPLE 3

Northern Blot Analysis of PICM-19 Cells

The RNA from STO mouse fibroblasts (CRL 1503 ATCC), PICM-16, ST pig testis cell line (CRL 1746 ATCC), 60-day fetal pig liver, adult pig liver and from PICM-19 cells grown in static culture for various periods after passage was analyzed by Northern analysis (Fourney et al., *Focus*, 10: 5–6, 1988). Twenty mg of total RNA, prepared as described by Chomczynski and Sacchi (*Anal. Biochem.*, 162: 156–159, 1987), was loaded per lane and transferred to Zetaprobe membrane (Bio-Rad). The Northern blot was hybridized successively with $^{32}$P-labeled cDNA probes to pig AFP and pig albumin, followed by autoradiography. Hybridization with a human glyceraldehyde-3-phosphate dehydrogenase DNA probe (pSP6-G3PDH, Ambion) was perfomed as a mRNA loading control.

Figure 9A:
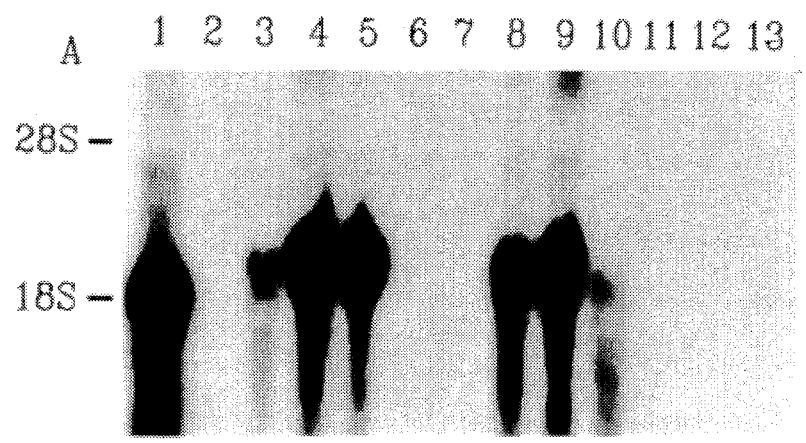
FIG. 9A–9C is a photograph of a Northern blot analysis of PICM-19 AFP and albumin expression. The Northern blot was hybridized successively with $^{32}$P-labeled cDNA probes to (A) pig AFP and (B) pig albumin, followed by autoradiography. Arrows indicate the positions of 28S and 18S RNA. Both cDNA probes detected a single band approximately 2 kb in length. Hybridization with a human glyceraldehyde-3-phosphate dehydrogenase (G3PDH) DNA probe was performed as an mRNA loading control (C). A single band of approximately 1.4 kb was detected by the G3PDH probe. In vivo fetal liver, lane 1; blank, lane 2; PICM-19 at 7, 15 and 23 days post-passage, lanes 3, 4 and 5, respectively; ST pig testis cell line, lane 6; PICM-16, lane 7; PICM-19 at 12, 19 and 31 days post-passage, lanes 8, 9 and 10, respectively; STO embryonic mouse fibroblasts, lane 11; blank, lane 12; and in vivo adult liver, lane 13.
Figure 9B:
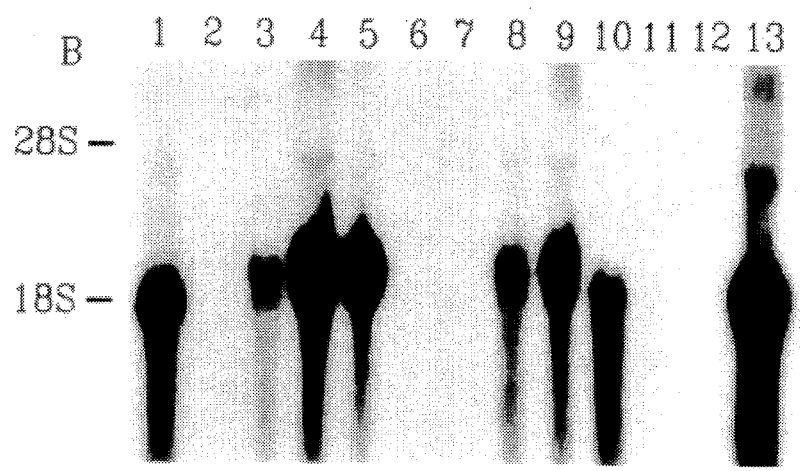
Figure 9C:

It was previously demonstrated that porcine parenchymal hepatocytes expressed a variety of genes specific to liver function, such as AFP and albumin (Stone, R. T., *J. Anim. Sci.*, 67: 1082–1089, 1989). These two proteins in particular are diagnostic for fetal hepatocyte character since normal AFP expression was restricted to fetal livers (Stone, 1989, supra). Moreover, these proteins are expressed during various early stages of hepatic stem cell development (Sigal et al., 1992, supra). Total RNA of PICM-19 cells was assayed by Northern blot, and high levels of AFP and albumin mRNA were detected (FIG. 9). The expression of the two genes was minimal in cultures that had recently been passaged (FIG. 9, lanes 3 and 8). The expression of AFP and albumin reached a peak in PICM-19 cultures that had remained in static culture for 2 to 3 weeks and had extensively differentiated into ductal structures (FIG. 9, lanes 4 and 9). A relatively high expression was maintained in culture for an additional 1 to 2 weeks although some loss of the AFP and albumin signal was seen after longer periods in culture (FIG. 9, lanes 5 and 10). Total RNA preparations from fetal and adult pig liver demonstrated that, as expected, AFP expression was restricted to fetal liver while albumin expression was found in both fetal and adult livers (FIG. 9, lanes 1 and 13). A pig testis epithelial cell line, an epiblast-derived epithelial cell line, PICM-16, analogous to MDCK epithelial cells, and STO feeder cells were all negative for AFP and albumin mRNA expression (FIG. 9, lanes 6, 7, and 11). The expression profile is consistent with PICM-19 cells being fetal hepatocytes (Stone, 1989, supra).

EXAMPLE 4

Immunoblot Analysis of PICM-19 Conditioned Medium

Serum-free medium [DMEM-199 with HGF (2 ng/ml), rat tail collagen (30 mg/ml), and 1×MITO$^+$ serum extender (Collaborative)] was conditioned for 3 days by 50–75% confluent monolayers of PICM-19 or STO feeder cells alone. Conditioned media samples or diluted pig serum (1:50) were mixed 1:1 with loading buffer containing SDS and 2-mercaptoethanol. Samples were loaded onto a 12% polyacrylamide gradient gel and electrophoresis performed under described conditions (Laemmli, U. K., *Nature*, 277:680–685, 1970). Proteins were transferred to nitrocellulose (0.2µ), blocked with gelatin and probed with polyclonal antisera. Specific immunoreactive antigens were visualized with alkaline phosphatase conjugated secondary antibody reagents (Sigma).

Figure 10:
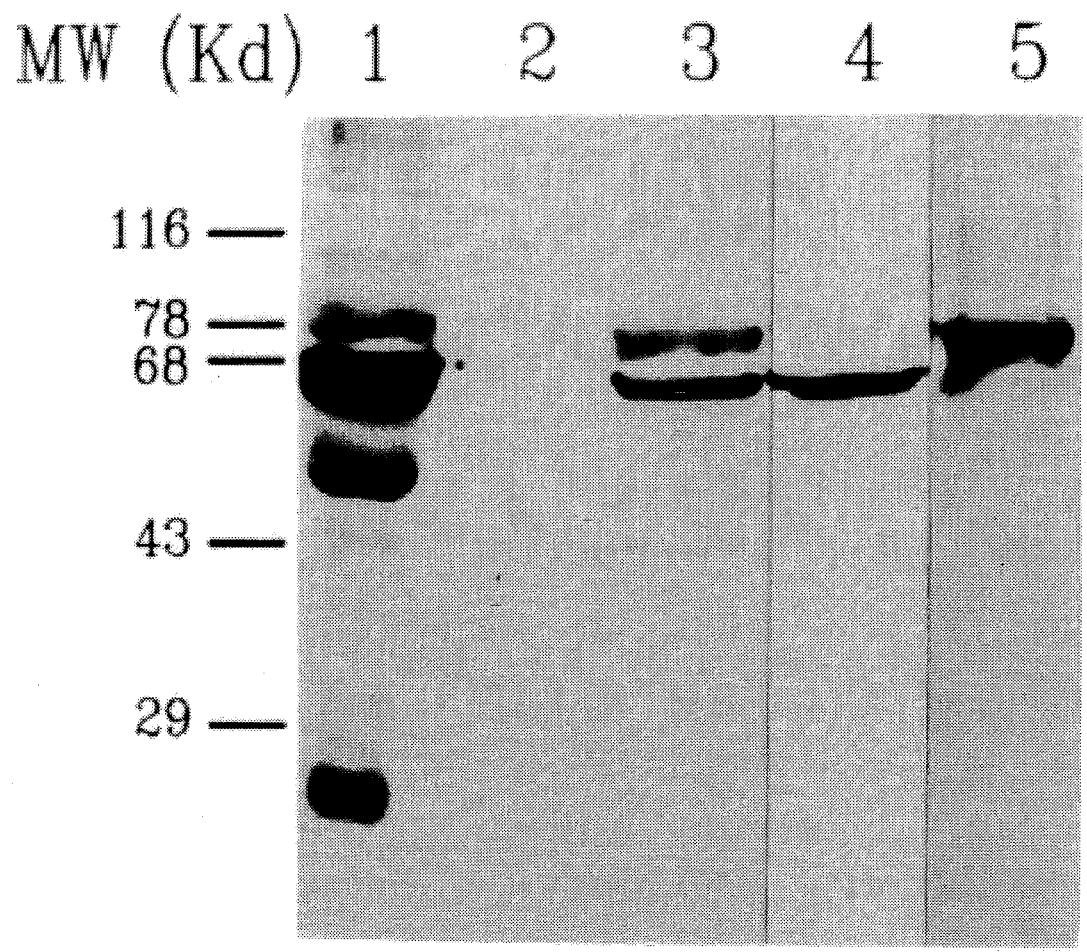
FIG. 10 is a photograph of an immunoblot analysis of PICM-19 transferrin and albumin secretion. Anti-whole pig serum (lanes 1, 2 and 3), anti-pig albumin (lane 4) and anti-pig transferrin (lane 5). Adult pig serum, lane 1; STO embryonic mouse fibroblast conditioned medium, lane 2; PICM-19 conditioned medium, lanes 3, 4 and 5. Serum-free medium [DMEM-199 with HGF (2 ng/ml), rat tail collagen (30 um/ml), and 1×MITO$^+$ serum extender (Collaborative)] was conditioned for 3 days by 50–75% confluent monolayers of PICM-19 or STO feeder cells alone.

PICM-19 secreted large amounts of transferrin and albumin into the serum-free culture medium. Coincident STO feeder cells alone were compared as a control for STO cell secretory activity and for nonspecific protein residues remaining from the initial 10% fetal bovine serum (FBS) culture of the cells. The unconcentrated conditioned media were analyzed by SDS-PAGE and immunoblotting (FIG. 10). PICM-19 cells secreted several proteins that crossreacted with an antisera to whole pig serum (FIG. 10, lane 3). The two prominent protein bands were subsequently identified as albumin and transferrin based on apparent molecular weight and crossreactivity with specific antisera to porcine albumin and transferrin (FIG. 10, lanes 4 and 5). In contrast, the STO feeder cell conditioned medium showed little or no reaction with the antibodies (FIG. 10, lane 2), demonstrating that the transferrin and albumin resulted from PICM-19 secretory activity.

EXAMPLE 5

TGFβ1 Inhibition of PICM-19 Cells

PICM-19 cells were plated at 1×10$^5$ cell/cm$^2$ in 4-well plates with 1.9 cm$^2$ well surfaces (Nunc) that had been previously seeded with 5×10$^4$ mitomycin-treated STO cells per cm$^2$. Porcine TGFβ1 (R&D Systems) was added at the indicated concentrations in 10% DMEM-199(+) at input and every 48–72 hours with refeedings. Cells were harvested after 7 days by trypsin-EDTA treatment and counted on a hemocytometer from 4 independent wells for each treatment. Cell counts were analyzed by ANOVA. Significant differences from control wells were determined by Dunnetts "T" procedure.

Figure 11:
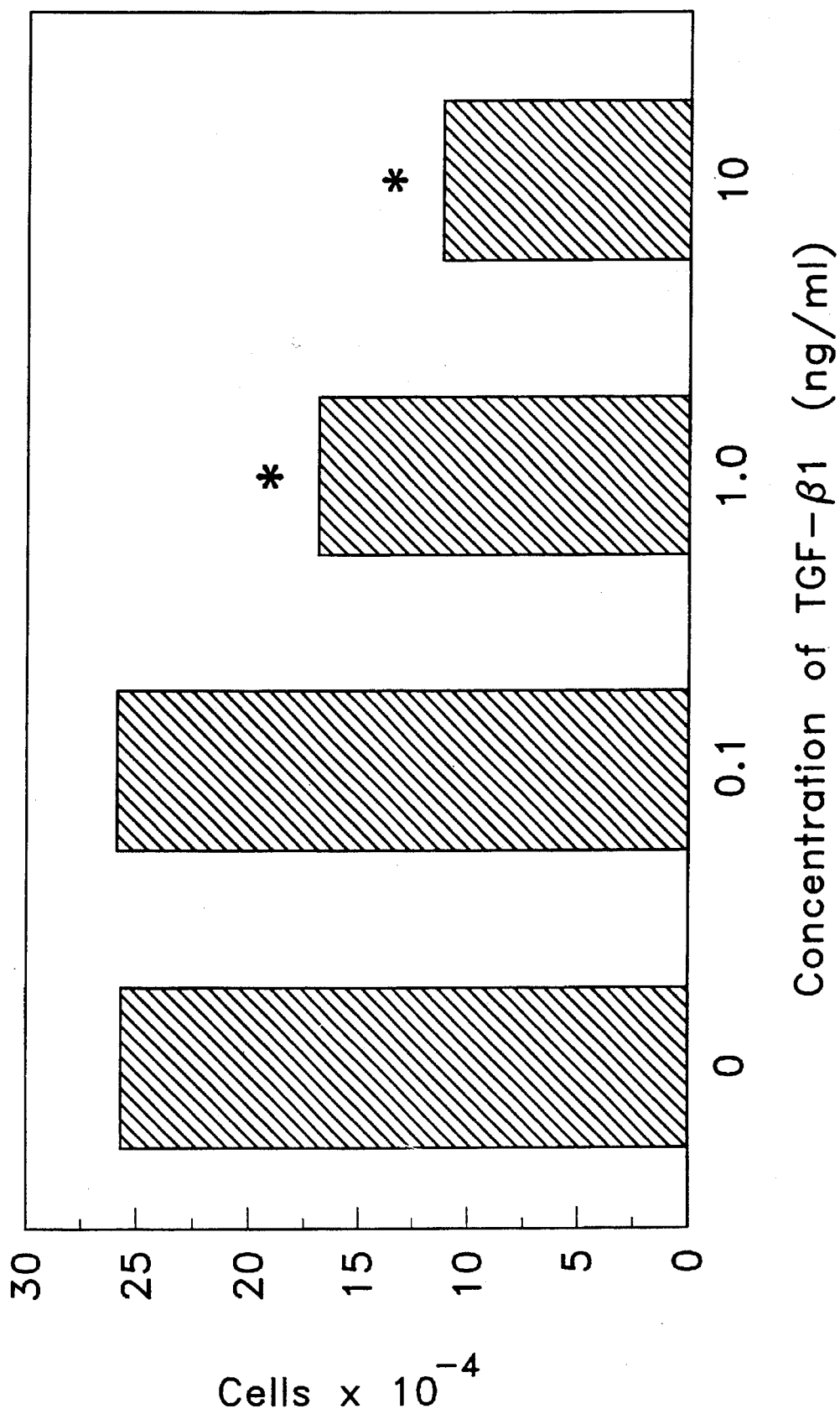
FIG. 11 shows TGFβ1 inhibition of PICM-19 cell growth and viability. Cell counts were analyzed by ANOVA. Significant differences from control wells were determined by Dunnetts "T" procedure. At 0.1 ng/ml the effect on PICM-19 cell growth and viability was no different (P>0.05) from that of the control medium not containing TGFβ1.

DNA synthesis in adult rat parenchymal hepatocytes was shown to be inhibited by TGFβ (Nakamura et al., *Biochem. Biophys. Res. Commun.*, 133: 1042–1060, 1985; Carr et al., *Cancer Res.*, 46: 2330–2334, 1986). Addition of porcine TGFβ1 inhibited the growth and viability of the PICM-19 cells (FIG. 11). PICM-19 cells that survived TGFβ1 (1 ng/ml) treatment for 7 days were enlarged, flattened, and elongated. Continued incubation with TGFβ1 (1 ng/ml) for 2 to 3 weeks resulted in the complete loss of the PICM-19 cells from the culture as judged by microscopic observation.

In summary, the parenchymal hepatocytes are not easily sustained in culture (Guguen-Guillouzo et al., 1983, supra; Perraud et al., 1991, supra; Tong et al., *Exp. Cell. Res.,* 200: 326–332, 1992), since the PICM hepatocyte cells have been shown to be strictly feeder-dependent and senesced if plated at split ratios higher than 1:5 off feeder cells. The PICM hepatocyte cells grew on top of or intermingled with the feeder-layer cells (FIG. 8), and all the cultures grew slowly. PICM-19 had a doubling time of approximately 72 hours by standard culture enumeration and by counting the cells of individual colonies. PICM-19 has been in continuous culture for over 2 years, representing over 100 population doublings, assuming a 100% plating efficiency at each passage. Over the course of this period, single-cell cloning of PICM-19 was performed at least six times with the establishment of mass cultures of the subclones. The differentiation potential of the cells did not change over the passage history of the PICM-19 culture. The subclones of PICM-19 also retained the ability to form canaliculi and ductal structures and to accumulate cellular and extracellular lipid. The morphology of the undifferentiated PICM-19 cells remained the same with no signs of senescence during the continuous culture of subclonings. Therefore the PICM-19 cell culture is an infinitely self-renewing cell population, i.e., a cell line.

The PICM hepatocyte cell cultures were all derived by co-culture on STO feeder cells. STO feeder cells were shown to provide an environment suitable for the isolation and maintenance of hepatocarcinoma cells (Aden et al., *Nature (London),* 282: 615–616, 1979), mouse embryonic stem cells (Robertson, 1987, supra) and mouse primordial germ cells (Matsui et al., *Cell,* 70: 841–847, 1992; Resnick et al., *Nature,* 359: 550–551, 1992). The STO feeder cells were shown to produce a variety of growth factors (Robertson, 1987, supra; Matsui, 1992, supra; Schmitt et al., 1991, supra; Montesano et al., 1991, supra; Montesano et al., *Cell,* 66: 697–711, 1991; Hilton et al., *J. Cell Physiol.,* 146: 207–215, 1991). Some of these were mediators of hepatocyte growth and function such as LIF and HGF (Montesano et al., (67) 1991, supra; Montesano, (66), 1991, supra; Hilton et al. 1991, supra). Hepatocytes were shown to express receptors for both LIF and HGF (Hilton, 1991, supra; Prat et al., *Int. J. Cancer,* 49: 323–328, 1991). LIF was reported to induce acute phase response proteins in hepatocytes (Baumann and Wong, *J. Immunol.,* 143, 1163–1168, 1989), and HGF has been widely described as a potent hepatocyte mitogen (Zarnegar and Michalopoulos, *Cancer Res.,* 49: 3314–3320, 1989; Strain et al., *J. Clin. Invest,,* 87: 1853–1857, 1991; Nakamura et al., *Biochem. Biophys. Res. Commun.,* 122: 1450–1459, 1984). Both LIF and HGF stimulated ($p > 0.05$) replication of PICM-19 cells when assayed in a 5% FBS and reduced STO feeder cell environment. Thus, two growth factors directly related to hepatocyte growth and function are present in the STO feeder layer and may support the development of hepatocytes from the primary epiblast culture.

The PICM-19 cell culture is the only known example of a sustainable culture of pluripotent parenchymal hepatocytes. Their fetal phenotype and their ability to differentiate into ductal structures, adipogenic cells, and monolayers of larger polygonal cells indicate that the PICM cells represent early hepatocyte progenitors (Sigal et al. 1992, supra; Fausto and Meade, 1989, supra). Their establishment in secondary or infinite culture may not reflect some characteristic of vitality which is peculiar to their epiblast source. The STO co-culture also supported the cultivation of hepatocytes from the 26-day pig fetal liver. These cell cultures formed monolayers of polygonal cells with interconnective canaliculi that could differentiate further to produce extracellular lipid or multicellular ductal structures. However, preliminary results indicate that the fetal liver-derived hepatocyte cultures are finite and senesce after variable degrees in in vitro passage. Thus, epiblast culture enables a derivation of fetal hepatocytes prior to differentiation into committed progenitor cells.

All references cited herein above are herein incorporated by reference.

We claim:

1. An isolated cell line of normal pluripotent parenchymal hepatocytes derived from a primary culture of pig epiblast cells.

2. The cell line of claim 1, where said cell line has all the identifying characteristics of PICM-19, ATCC No. CRL 11519.

3. A method of preparing a cell line from the epiblast of the pig blastocyst, wherein said cell line comprises normal pluripotent parenchymal hepatocytes, said method comprising, a) removing a blastocyst from the uterus of a pig, b) immunodissecting the inner cell mass from said blastocyst, c) dissecting the epiblast from the inner cell mass and culturing the epiblast for a time sufficient for colony formation, wherein a primary culture is obtained, d) subculturing the epiblast colonies, from step c) to obtain a secondary culture, and e) isolating said hepatocytes from the secondary culture of step d).

4. The method of claim 3, wherein said primary and said secondary cultures are grown on feeder layers.

5. The method of claim 4, wherein said feeder layers comprise STO feeder cells.

* * * * *